United States Patent
McCombs

(10) Patent No.: US 7,477,926 B2
(45) Date of Patent: Jan. 13, 2009

(54) METHODS AND APPARATUSES FOR PROVIDING A REFERENCE ARRAY INPUT DEVICE

(75) Inventor: Daniel L. McCombs, Memphis, TN (US)

(73) Assignee: Smith & Nephew, Inc., Memphis, TN (US)

(*) Notice: Subject to any disclaimer, the term of this patent is extended or adjusted under 35 U.S.C. 154(b) by 312 days.

(21) Appl. No.: 10/907,374

(22) Filed: Mar. 30, 2005

(65) Prior Publication Data

US 2005/0228266 A1   Oct. 13, 2005

Related U.S. Application Data

(60) Provisional application No. 60/557,872, filed on Mar. 31, 2004.

(51) Int. Cl.
*A61B 5/05* (2006.01)
(52) U.S. Cl. .................. 600/407; 600/414; 600/426
(58) Field of Classification Search ........... 600/407, 600/414, 426, 429; 382/128; 606/130; 345/156
See application file for complete search history.

(56) References Cited

U.S. PATENT DOCUMENTS

| 100,602 | A | 3/1870 | Coes |
| 1,076,971 | A | 10/1913 | Geiger |
| 1,201,467 | A | 10/1916 | Hoglund |
| 2,092,869 | A | 9/1937 | Baum |
| 3,412,733 | A | 11/1968 | Ross |
| 3,457,922 | A | 7/1969 | Ray |
| 3,702,611 | A | 11/1972 | Fishbein |
| 4,305,394 | A | 12/1981 | Bertuch, Jr. |
| 4,323,080 | A | 4/1982 | Melharty |
| 4,421,112 | A | 12/1983 | Mains et al. |
| 4,456,010 | A | 6/1984 | Reimels et al. |

(Continued)

FOREIGN PATENT DOCUMENTS

DE   042 25 112 C   12/1993

(Continued)

OTHER PUBLICATIONS

"Implant" Merriam-Webster Online Dictionary [online], Retrieved from the Internet <URL: www.m-w.com.

(Continued)

*Primary Examiner*—Eric F Winakur
*Assistant Examiner*—Michael T. Rozanski
(74) *Attorney, Agent, or Firm*—Kilpatrick Stockton LLP

(57) ABSTRACT

Methods and apparatuses for providing a reference array input device for use with a computer-aided surgical navigation system. A reference array input device according to an embodiment of the present invention is configured to provide a plurality of fiducial members comprising portions capable of being sensed by at least two sensors associated with the computer-aided surgical navigation system in order to determine position and orientation of the reference array input device by the system. The reference array input device can include a plurality of indicator detectors adapted to facilitate selection of a corresponding instruction associated with the computer-aided surgical navigation system. The reference array input device can also include a mount adapted to support the reference array input device adjacent to an object, a surgical instrument, or a joint replacement prosthesis.

46 Claims, 7 Drawing Sheets

U.S. PATENT DOCUMENTS

| | | |
|---|---|---|
| 4,457,307 A | 7/1984 | Stillwell |
| 4,483,554 A | 11/1984 | Ernst |
| 4,524,766 A | 6/1985 | Petersen |
| 4,534,364 A | 8/1985 | Lamoreux |
| 4,565,192 A | 1/1986 | Shapiro |
| 4,566,448 A | 1/1986 | Rohr, Jr. |
| 4,567,885 A | 2/1986 | Androphy |
| 4,567,886 A | 2/1986 | Petersen |
| 4,574,794 A | 3/1986 | Cooke et al. |
| 4,583,554 A | 4/1986 | Mittelman et al. |
| 4,671,275 A | 6/1987 | Deyerle |
| 4,703,751 A | 11/1987 | Pohl |
| 4,712,951 A | 12/1987 | Brown |
| 4,718,413 A | 1/1988 | Johnson |
| 4,722,056 A | 1/1988 | Roberts et al. |
| 4,738,256 A | 4/1988 | Freeman et al. |
| 4,759,350 A | 7/1988 | Dunn et al. |
| 4,768,504 A | 9/1988 | Ender |
| 4,777,942 A | 10/1988 | Frey et al. |
| 4,802,468 A | 2/1989 | Powlan |
| 4,803,976 A | 2/1989 | Frigg et al. |
| 4,809,689 A | 3/1989 | Anapliotis |
| 4,815,899 A | 3/1989 | Regan |
| 4,875,475 A | 10/1989 | Comte et al. |
| 4,892,093 A | 1/1990 | Zarnowski et al. |
| 4,913,163 A | 4/1990 | Roger et al. |
| 4,938,762 A | 7/1990 | Wehrli |
| 4,952,213 A | 8/1990 | Bowman et al. |
| 4,964,862 A | 10/1990 | Arms |
| 4,991,579 A | 2/1991 | Allen |
| 5,002,545 A | 3/1991 | Whiteside et al. |
| 5,002,578 A | 3/1991 | Luman |
| 5,016,639 A | 5/1991 | Allen |
| 5,037,423 A | 8/1991 | Kenna |
| 5,037,426 A | 8/1991 | Goble et al. |
| 5,049,149 A | 9/1991 | Schmidt |
| 5,053,039 A | 10/1991 | Hofmann et al. |
| 5,078,719 A | 1/1992 | Schreiber |
| 5,092,869 A | 3/1992 | Waldron |
| 5,094,241 A | 3/1992 | Allen |
| 5,097,839 A | 3/1992 | Allen |
| 5,098,426 A | 3/1992 | Sklar et al. |
| 5,116,338 A | 5/1992 | Poggie et al. |
| 5,119,817 A | 6/1992 | Allen |
| 5,122,144 A | 6/1992 | Bert et al. |
| 5,129,909 A | 7/1992 | Sutherland |
| 5,147,408 A | 9/1992 | Noble |
| 5,190,547 A | 3/1993 | Barber, Jr. et al. |
| 5,211,164 A | 5/1993 | Allen |
| 5,213,312 A | 5/1993 | MacDonald |
| 5,217,499 A | 6/1993 | Shelley |
| 5,230,338 A | 7/1993 | Allen et al. |
| 5,246,444 A | 9/1993 | Schreiber |
| 5,254,119 A | 10/1993 | Schreiber |
| 5,263,972 A | 11/1993 | Evans et al. |
| 5,289,826 A | 3/1994 | Kovacevic |
| 5,305,203 A | 4/1994 | Raab |
| 5,342,366 A | 8/1994 | Whiteside et al. |
| 5,360,016 A | 11/1994 | Kovacevic |
| 5,364,401 A | 11/1994 | Ferrante et al. |
| 5,364,402 A | 11/1994 | Mumme et al. |
| 5,365,996 A | 11/1994 | Crook |
| 5,375,588 A | 12/1994 | Yoon |
| 5,379,133 A | 1/1995 | Kirk |
| 5,383,454 A | 1/1995 | Bucholz |
| 5,387,218 A | 2/1995 | Meswania et al. |
| 5,389,101 A | 2/1995 | Heilbrun et al. |
| 5,395,376 A | 3/1995 | Caspari et al. |
| 5,397,329 A | 3/1995 | Allen |
| 5,403,320 A | 4/1995 | Luman |
| 5,423,828 A | 6/1995 | Benson |
| 5,425,355 A | 6/1995 | Kulick |
| 5,432,366 A | 7/1995 | Banerjee et al. |
| 5,445,166 A | 8/1995 | Taylor |
| 5,445,642 A | 8/1995 | McNulty et al. |
| 5,449,360 A | 9/1995 | Schreiber |
| 5,452,407 A | 9/1995 | Crook |
| 5,462,548 A | 10/1995 | Pappas et al. |
| 5,462,549 A | 10/1995 | Glock |
| 5,468,244 A | 11/1995 | Attfield et al. |
| 5,470,354 A | 11/1995 | Hershberger et al. |
| 5,474,559 A | 12/1995 | Bertin et al. |
| 5,484,437 A | 1/1996 | Michelson |
| 5,486,178 A | 1/1996 | Hodge |
| 5,490,854 A | 2/1996 | Fisher et al. |
| 5,491,510 A | 2/1996 | Gove |
| 5,507,824 A | 4/1996 | Lennox |
| 5,514,139 A | 5/1996 | Goldstein et al. |
| 5,517,990 A | 5/1996 | Kalfas et al. |
| 5,527,316 A | 6/1996 | Williamson |
| 5,540,691 A | 7/1996 | Elmstrom et al. |
| 5,540,694 A | 7/1996 | DeCarlo, Jr. |
| 5,540,695 A | 7/1996 | Levy |
| 5,540,696 A | 7/1996 | Booth, Jr. et al. |
| 5,569,260 A | 10/1996 | Petersen |
| 5,597,379 A | 1/1997 | Haines et al. |
| 5,598,269 A | 1/1997 | Kitaevich et al. |
| 5,603,318 A | 2/1997 | Heilbrun et al. |
| 5,613,969 A | 3/1997 | Jenkins, Jr. |
| 5,643,268 A | 7/1997 | Vilsmeier et al. |
| 5,643,272 A | 7/1997 | Haines et al. |
| 5,658,290 A | 8/1997 | Lechot |
| 5,669,914 A | 9/1997 | Eckhoff |
| 5,676,668 A | 10/1997 | McCue et al. |
| 5,681,316 A | 10/1997 | DeOrio et al. |
| 5,682,886 A | 11/1997 | Delp et al. |
| 5,683,397 A | 11/1997 | Vendrely et al. |
| 5,688,279 A | 11/1997 | McNulty et al. |
| 5,693,056 A | 12/1997 | Carls et al. |
| 5,695,501 A | 12/1997 | Carol et al. |
| 5,702,406 A | 12/1997 | Vilsmeier et al. |
| 5,704,941 A | 1/1998 | Jacober et al. |
| 5,707,370 A | 1/1998 | Berki et al. |
| 5,709,689 A | 1/1998 | Ferrante et al. |
| 5,715,836 A | 2/1998 | Kliegis et al. |
| 5,716,361 A | 2/1998 | Masini |
| 5,720,752 A | 2/1998 | Elliott et al. |
| 5,722,978 A | 3/1998 | Jenkins, Jr. |
| 5,733,292 A | 3/1998 | Gustilo et al. |
| 5,735,904 A | 4/1998 | Pappas |
| 5,743,915 A | 4/1998 | Bertin et al. |
| 5,748,767 A | 5/1998 | Raab |
| 5,755,725 A | 5/1998 | Druais |
| 5,755,803 A | 5/1998 | Haines et al. |
| 5,769,861 A | 6/1998 | Vilsmeier |
| 5,772,593 A | 6/1998 | Hakamata |
| 5,772,594 A | 6/1998 | Barrick |
| 5,776,064 A | 7/1998 | Kalfas et al. |
| 5,782,842 A | 7/1998 | Kloess et al. |
| 5,792,147 A | 8/1998 | Evans et al. |
| 5,797,924 A | 8/1998 | Schulte et al. |
| 5,799,055 A | 8/1998 | Peshkin et al. |
| 5,800,352 A | 9/1998 | Ferre et al. |
| 5,800,438 A | 9/1998 | Tuke et al. |
| 5,807,252 A | 9/1998 | Hassfeld et al. |
| 5,810,827 A | 9/1998 | Haines et al. |
| 5,810,841 A | 9/1998 | McNeirney et al. |
| 5,817,097 A | 10/1998 | Howard et al. |
| 5,830,214 A | 11/1998 | Flom et al. |
| 5,836,954 A | 11/1998 | Heilbrun et al. |
| 5,848,967 A | 12/1998 | Cosman |
| 5,850,836 A | 12/1998 | Steiger et al. |
| 5,860,981 A | 1/1999 | Bertin et al. |
| 5,865,809 A | 2/1999 | Moenning et al. |

| | | | | | | |
|---|---|---|---|---|---|---|
| 5,871,018 | A | 2/1999 | Delp et al. | 6,200,316 B1 | 3/2001 | Zwirkoski et al. |
| 5,871,445 | A | 2/1999 | Bucholz | 6,205,411 B1 | 3/2001 | DiGioia, III et al. |
| 5,879,352 | A | 3/1999 | Filoso et al. | 6,211,976 B1 | 4/2001 | Popovich et al. |
| 5,879,354 | A | 3/1999 | Haines et al. | 6,214,011 B1 | 4/2001 | Masini |
| 5,880,976 | A | 3/1999 | DiGioia, III et al. | 6,216,029 B1 | 4/2001 | Paltieli |
| 5,885,296 | A | 3/1999 | Masini | 6,223,067 B1 | 4/2001 | Vilsmeier et al. |
| 5,885,297 | A | 3/1999 | Matsen, III | 6,226,548 B1 | 5/2001 | Foley et al. |
| 5,897,559 | A | 4/1999 | Masinie | 6,228,090 B1 | 5/2001 | Waddell |
| 5,916,221 | A | 6/1999 | Hodorek et al. | 6,228,092 B1 | 5/2001 | Mikhail |
| 5,920,395 | A | 7/1999 | Schulz | 6,235,038 B1 | 5/2001 | Hunter et al. |
| 5,921,992 | A | 7/1999 | Costales et al. | 6,236,875 B1 | 5/2001 | Bucholz et al. |
| 5,925,049 | A | 7/1999 | Gustilo et al. | 6,241,735 B1 | 6/2001 | Marmulla |
| 5,935,128 | A | 8/1999 | Carter et al. | 6,249,581 B1 | 6/2001 | Kok |
| 5,938,665 | A | 8/1999 | Martin | 6,258,095 B1 | 7/2001 | Lombardo et al. |
| 5,944,722 | A | 8/1999 | Masini | 6,258,096 B1 | 7/2001 | Seki |
| 5,947,971 | A | 9/1999 | Kuslich et al. | 6,264,647 B1 | 7/2001 | Lechot |
| 5,947,973 | A | 9/1999 | Masini | 6,283,971 B1 | 9/2001 | Temeles |
| 5,951,561 | A | 9/1999 | Pepper et al. | 6,285,902 B1 | 9/2001 | Kienzle, III et al. |
| 5,957,926 | A | 9/1999 | Masini | 6,295,513 B1 | 9/2001 | Thackston |
| 5,961,523 | A | 10/1999 | Masini | 6,317,616 B1 | 11/2001 | Glossop |
| 5,971,989 | A | 10/1999 | Masini | 6,319,256 B1 | 11/2001 | Spotorno |
| 5,980,526 | A | 11/1999 | Johnson et al. | 6,332,891 B1 | 12/2001 | Himes |
| 5,980,535 | A | 11/1999 | Barnett et al. | 6,333,971 B2 | 12/2001 | McCrory et al. |
| 5,999,837 | A | 12/1999 | Messner et al. | 6,344,853 B1 | 2/2002 | Knight |
| 6,001,106 | A | 12/1999 | Ryan et al. | 6,347,240 B1 | 2/2002 | Foley et al. |
| 6,002,859 | A | 12/1999 | DiGioia, III et al. | 6,351,659 B1 | 2/2002 | Vilsmeier |
| 6,006,126 | A | 12/1999 | Cosman | 6,351,661 B1 | 2/2002 | Cosman |
| 6,006,127 | A | 12/1999 | Van Der Brug et al. | 6,377,839 B1 | 4/2002 | Kalfas et al. |
| 6,007,537 | A | 12/1999 | Burkinshaw et al. | 6,383,188 B2 | 5/2002 | Kuslich et al. |
| 6,010,506 | A | 1/2000 | Gosney et al. | 6,385,475 B1 | 5/2002 | Cinquin et al. |
| 6,011,987 | A | 1/2000 | Barnett | 6,405,072 B1 | 6/2002 | Cosman |
| 6,016,606 | A | 1/2000 | Oliver et al. | 6,413,261 B1 | 7/2002 | Grundei |
| 6,021,342 | A | 2/2000 | Brabrand | 6,434,507 B1 | 8/2002 | Clayton et al. |
| 6,021,343 | A | 2/2000 | Foley et al. | 6,440,140 B2 | 8/2002 | Bullivant et al. |
| 6,022,377 | A | 2/2000 | Nuelle et al. | 6,443,956 B1 | 9/2002 | Ray |
| 6,026,315 | A | 2/2000 | Lenz et al. | 6,451,059 B1 | 9/2002 | Janas et al. |
| 6,030,391 | A | 2/2000 | Brainard et al. | 6,458,135 B1 | 10/2002 | Harwin et al. |
| 6,033,410 | A | 3/2000 | McLean et al. | 6,463,351 B1 | 10/2002 | Clynch |
| 6,041,249 | A | 3/2000 | Regn | 6,468,202 B1 | 10/2002 | Irion et al. |
| 6,044,291 | A | 3/2000 | Rockseisen | 6,477,400 B1 | 11/2002 | Barrick |
| 6,045,556 | A | 4/2000 | Cohen | 6,478,799 B1 | 11/2002 | Williamson |
| 6,050,724 | A | 4/2000 | Schmitz et al. | 6,484,049 B1 | 11/2002 | Seeley et al. |
| 6,053,922 | A | 4/2000 | Krause et al. | 6,490,467 B1 | 12/2002 | Bucholz et al. |
| 6,056,756 | A | 5/2000 | Eng et al. | 6,491,429 B1 | 12/2002 | Suhm |
| 6,068,633 | A | 5/2000 | Masini | 6,491,702 B2 | 12/2002 | Heilbrun et al. |
| 6,069,932 | A | 5/2000 | Peshkin et al. | 6,503,249 B1 | 1/2003 | Krause |
| 6,073,044 | A | 6/2000 | Fitzpatrick et al. | 6,503,254 B2 | 1/2003 | Masini |
| 6,077,269 | A | 6/2000 | Masini | 6,527,443 B1 | 3/2003 | Vilsmeier et al. |
| 6,081,336 | A | 6/2000 | Messner et al. | 6,540,739 B2 | 4/2003 | Lechot |
| 6,083,163 | A | 7/2000 | Wegner et al. | 6,546,279 B1 | 4/2003 | Bova et al. |
| 6,096,048 | A | 8/2000 | Howard et al. | 6,551,319 B2 | 4/2003 | Lieberman |
| 6,102,916 | A | 8/2000 | Masini | 6,551,324 B2 | 4/2003 | Muller |
| 6,132,433 | A | 10/2000 | Whelan | 6,551,325 B2 | 4/2003 | Neubauer et al. |
| 6,143,390 | A | 11/2000 | Takamiya et al. | 6,554,837 B1 | 4/2003 | Hauri et al. |
| 6,144,875 | A | 11/2000 | Schweikard et al. | 6,558,391 B2 | 5/2003 | Axelson, Jr. et al. |
| 6,146,390 | A | 11/2000 | Heilbrun et al. | 6,558,421 B1 | 5/2003 | Fell et al. |
| 6,148,280 | A | 11/2000 | Kramer | 6,567,687 B2 | 5/2003 | Front et al. |
| 6,161,033 | A | 12/2000 | Kuhn | 6,574,493 B2 | 6/2003 | Rasche et al. |
| 6,162,190 | A | 12/2000 | Kramer | 6,595,997 B2 | 7/2003 | Axelson, Jr. et al. |
| 6,165,181 | A | 12/2000 | Heilbrun et al. | 6,602,259 B1 | 8/2003 | Masini |
| 6,167,145 | A | 12/2000 | Foley et al. | 6,620,168 B1 | 9/2003 | Lombardo et al. |
| 6,167,292 | A | 12/2000 | Badano et al. | 6,620,268 B2 | 9/2003 | Cho et al. |
| 6,167,295 | A | 12/2000 | Cosman | 6,640,127 B1 | 10/2003 | Kosaka et al. |
| 6,167,296 | A | 12/2000 | Shahidi | 6,652,142 B2 | 11/2003 | Launay et al. |
| 6,168,627 | B1 | 1/2001 | Huebner | 6,662,036 B2 | 12/2003 | Cosman |
| 6,174,335 | B1 | 1/2001 | Varieur | 6,673,077 B1 | 1/2004 | Katz |
| 6,185,315 | B1 | 2/2001 | Schmucker et al. | 6,675,040 B1 | 1/2004 | Cosman |
| 6,187,010 | B1 | 2/2001 | Masini | 6,685,711 B2 | 2/2004 | Axelson, Jr. et al. |
| 6,190,320 | B1 | 2/2001 | Lelong | 6,690,964 B2 | 2/2004 | Bieger et al. |
| 6,190,395 | B1 | 2/2001 | Williams | 6,692,447 B1 | 2/2004 | Picard |
| 6,195,168 | B1 | 2/2001 | De Lega et al. | 6,695,848 B2 | 2/2004 | Haines |
| 6,197,064 | B1 | 3/2001 | Haines et al. | 6,702,821 B2 | 3/2004 | Bonutti |
| 6,198,794 | B1 | 3/2001 | Peshkin et al. | 6,711,431 B2 | 3/2004 | Sarin et al. |

| | | |
|---|---|---|
| 6,712,823 B2 | 3/2004 | Grusin et al. |
| 6,712,824 B2 | 3/2004 | Millard et al. |
| 6,716,249 B2 | 4/2004 | Hyde |
| 6,718,194 B2 | 4/2004 | Kienzle |
| 6,725,080 B2 | 4/2004 | Melkent et al. |
| 6,725,082 B2 | 4/2004 | Sati et al. |
| 6,728,599 B2 | 4/2004 | Wang et al. |
| 6,772,026 B2 | 8/2004 | Bradbury et al. |
| 6,780,190 B2 | 8/2004 | Maroney |
| 6,785,593 B2 | 8/2004 | Wang |
| 6,799,088 B2 | 9/2004 | Wang |
| 6,814,490 B1 | 11/2004 | Suhm et al. |
| 6,827,723 B2 | 12/2004 | Carson |
| 6,836,703 B2 | 12/2004 | Wang |
| 6,871,117 B2 | 3/2005 | Wang |
| 6,882,982 B2 | 4/2005 | McMenimen |
| 6,892,112 B2 | 5/2005 | Wang |
| 6,905,514 B2 | 6/2005 | Carignan et al. |
| 6,923,817 B2 | 8/2005 | Carson |
| 6,947,786 B2 | 9/2005 | Simon et al. |
| 6,993,374 B2 | 1/2006 | Sasso |
| 7,001,346 B2 | 2/2006 | White |
| 7,035,702 B2 | 4/2006 | Jelonek et al. |
| 7,237,556 B2 | 7/2007 | Smothers |
| 7,241,298 B2 | 7/2007 | Nemec et al. |
| 2001/0001120 A1 | 5/2001 | Masini |
| 2001/0014772 A1 | 8/2001 | Lampotang et al. |
| 2001/0016745 A1 | 8/2001 | Bullivant et al. |
| 2001/0034530 A1 | 10/2001 | Malackowski et al. |
| 2001/0036245 A1 | 11/2001 | Kienzle, III et al. |
| 2001/0039421 A1 | 11/2001 | Heilbrun et al. |
| 2002/0002330 A1 | 1/2002 | Vilsmeier |
| 2002/0002365 A1 | 1/2002 | Lechot |
| 2002/0007294 A1 | 1/2002 | Bradbury, et al. |
| 2002/0011594 A1 | 1/2002 | DeSouza |
| 2002/0016540 A1 | 2/2002 | Mikus et al. |
| 2002/0018981 A1 | 2/2002 | Andersson et al. |
| 2002/0029041 A1 | 3/2002 | Hover et al. |
| 2002/0032451 A1 | 3/2002 | Tierney et al. |
| 2002/0038085 A1 | 3/2002 | Immerz |
| 2002/0052606 A1 | 5/2002 | Bonutti |
| 2002/0065461 A1 | 5/2002 | Cosman |
| 2002/0068942 A1 | 6/2002 | Neubauer et al. |
| 2002/0072748 A1 | 6/2002 | Robioneck |
| 2002/0072821 A1 | 6/2002 | Baker |
| 2002/0077533 A1 | 6/2002 | Bieger et al. |
| 2002/0077540 A1 | 6/2002 | Kienzle, III |
| 2002/0085681 A1 | 7/2002 | Jensen |
| 2002/0087101 A1 | 7/2002 | Barrick et al. |
| 2002/0095081 A1 | 7/2002 | Vilsmeier |
| 2002/0102214 A1 | 8/2002 | Briley-Saebo et al. |
| 2002/0107518 A1 | 8/2002 | Neubauer et al. |
| 2002/0115934 A1 | 8/2002 | Tuke |
| 2002/0133161 A1 | 9/2002 | Axelson et al. |
| 2002/0133175 A1 | 9/2002 | Carson |
| 2002/0147455 A1 | 10/2002 | Carson |
| 2002/0151894 A1 | 10/2002 | Melkent et al. |
| 2002/0151898 A1 | 10/2002 | Sohngen et al. |
| 2002/0156371 A1 | 10/2002 | Hedlund et al. |
| 2002/0156479 A1 | 10/2002 | Schulzki et al. |
| 2002/0188194 A1 | 12/2002 | Cosman |
| 2002/0193800 A1 | 12/2002 | Kienzle, III et al. |
| 2002/0198448 A1 | 12/2002 | Zuk et al. |
| 2002/0198451 A1 | 12/2002 | Carson |
| 2002/0198531 A1 | 12/2002 | Millard et al. |
| 2003/0006107 A1 | 1/2003 | Thompson |
| 2003/0018338 A1 | 1/2003 | Axelson, Jr. et al. |
| 2003/0045883 A1 | 3/2003 | Chow et al. |
| 2003/0050643 A1 | 3/2003 | Taft |
| 2003/0030787 A1 | 4/2003 | Bradbury |
| 2003/0069591 A1 | 4/2003 | Carson |
| 2003/0073901 A1 | 4/2003 | Simon et al. |
| 2003/0153829 A1 | 8/2003 | Sarin et al. |
| 2003/0153859 A1 | 8/2003 | Hinshon |
| 2003/0153978 A1 | 8/2003 | Whiteside |
| 2003/0164172 A1 | 9/2003 | Chumas et al. |
| 2003/0181918 A1 | 9/2003 | Smothers et al. |
| 2003/0187351 A1 | 10/2003 | Franck et al. |
| 2003/0187452 A1 | 10/2003 | Smith et al. |
| 2003/0192557 A1 | 10/2003 | Krag et al. |
| 2003/0225329 A1 | 12/2003 | Rossner et al. |
| 2004/0019382 A1 | 1/2004 | Amirouche et al. |
| 2004/0030237 A1 | 2/2004 | Lee et al. |
| 2004/0030245 A1 | 2/2004 | Noble et al. |
| 2004/0054489 A1 | 3/2004 | De La Barrera |
| 2004/0073279 A1 | 4/2004 | Malackowski et al. |
| 2004/0087852 A1 | 5/2004 | Chen et al. |
| 2004/0097952 A1 | 5/2004 | Sarin et al. |
| 2004/0152972 A1 | 8/2004 | Hunter et al. |
| 2004/0153081 A1 | 8/2004 | Tulkis |
| 2004/0153083 A1 | 8/2004 | Nemec et al. |
| 2004/0167391 A1 | 8/2004 | Solar et al. |
| 2004/0171924 A1 | 9/2004 | Mire et al. |
| 2004/0243481 A1 | 12/2004 | Bradbury et al. |
| 2004/0254586 A1 | 12/2004 | Sarin |
| 2004/0260290 A1 | 12/2004 | Zander et al. |
| 2005/0021037 A1 | 1/2005 | McCombs et al. |
| 2005/0021043 A1 | 1/2005 | Jansen |
| 2005/0075632 A1 | 4/2005 | Russel et al. |
| 2005/0085715 A1 | 4/2005 | Dukesherer et al. |
| 2005/0085822 A1 | 4/2005 | Thornberry et al. |
| 2005/0101966 A1 | 5/2005 | Lavailee |
| 2005/0109855 A1 | 5/2005 | McCombs |
| 2005/0113658 A1 | 5/2005 | Jacobson et al. |
| 2005/0113659 A1 | 5/2005 | Pothier |
| 2005/0113846 A1 | 5/2005 | Carson |
| 2005/0119639 A1 | 6/2005 | McCombs |
| 2005/0119777 A1 | 6/2005 | Arbogast et al. |
| 2005/0124988 A1 | 6/2005 | Terrill-Grisoni et al. |
| 2005/0148843 A1 | 7/2005 | Roose |
| 2005/0149003 A1 | 7/2005 | Tierney et al. |
| 2005/0149041 A1 | 7/2005 | McGinley |
| 2005/0154331 A1 | 7/2005 | Christie et al. |
| 2005/0159759 A1 | 7/2005 | Harbaugh et al. |
| 2005/0177172 A1 | 8/2005 | Acker |
| 2005/0197569 A1 | 9/2005 | McCombs |
| 2005/0197814 A1 | 9/2005 | Aram et al. |
| 2005/0203384 A1 | 9/2005 | Sati et al. |
| 2005/0209726 A1 | 9/2005 | Voit et al. |
| 2005/0216305 A1 | 9/2005 | Funderud |
| 2005/0228266 A1 | 10/2005 | McCombs |
| 2005/0228404 A1 | 10/2005 | Vandevelde |
| 2005/0234332 A1 | 10/2005 | Murphy |
| 2005/0234465 A1 | 10/2005 | McCombs |
| 2005/0234466 A1 | 10/2005 | Stallings |
| 2005/0234468 A1 | 10/2005 | Carson |
| 2005/0245808 A1 | 11/2005 | Carson |
| 2005/0279368 A1 | 12/2005 | McCombs |
| 2005/0288676 A1 | 12/2005 | Schnieders |
| 2006/0015120 A1 | 1/2006 | Richard et al. |
| 2006/0161051 A1 | 7/2006 | Terrill-Grisoni et al. |
| 2006/0190011 A1 | 8/2006 | Ries |
| 2006/0200025 A1 | 9/2006 | Elliott |
| 2006/0229626 A1 | 10/2006 | Kelman |
| 2007/0118055 A1 | 5/2007 | McCombs |
| 2007/0123912 A1 | 5/2007 | Carson |
| 2007/0169782 A1 | 7/2007 | Castleman |

FOREIGN PATENT DOCUMENTS

| | | |
|---|---|---|
| DE | 296 00 990 | 1/1996 |
| DE | 196 29 011 A1 | 1/1998 |
| DE | 197 09 960 A | 9/1998 |
| DE | 299 06 438 U1 | 9/1999 |
| DE | 296 23 941 U1 | 11/2000 |
| DE | 200 21 494 | 3/2001 |

| | | | |
|---|---|---|---|
| DE | 201 03 416 I1 | 7/2001 |
| DE | 100 12 042 | 8/2001 |
| DE | 100 31 887 A1 | 1/2002 |
| DE | 102 07 035 | 2/2002 |
| DE | 100 45 381 A1 | 4/2002 |
| DE | 202 13 243 | 10/2002 |
| DE | 203 09 399 | 8/2003 |
| EP | 0 327 509 A1 | 8/1989 |
| EP | 0 327 509 B1 | 8/1989 |
| EP | 0 337 901 A1 | 10/1989 |
| EP | 0 340 176 A2 | 11/1989 |
| EP | 0 216 794 B1 | 12/1989 |
| EP | 0 366 488 B1 | 5/1990 |
| EP | 0 376 657 B1 | 7/1990 |
| EP | 0 380 451 A2 | 8/1990 |
| EP | 0 415 837 A2 | 3/1991 |
| EP | 0 466 659 A2 | 1/1992 |
| EP | 0 359 097 | 8/1992 |
| EP | 0 538 152 A1 | 4/1993 |
| EP | 0 538 153 B1 | 4/1993 |
| EP | 0 555 003 B1 | 8/1993 |
| EP | 0 428 303 | 7/1995 |
| EP | 0 676 178 A | 10/1995 |
| EP | 0 720 834 A2 | 7/1996 |
| EP | 0 619 097 | 6/1999 |
| EP | 1 149 562 A2 | 10/2001 |
| EP | 1 033 108 | 2/2002 |
| EP | 1 190 676 B1 | 3/2002 |
| EP | 1 226 788 | 7/2002 |
| EP | 1 226 788 A1 | 7/2002 |
| EP | 0 782 842 | 9/2002 |
| EP | 1 236 450 A1 | 9/2002 |
| EP | 1 249 207 | 10/2002 |
| EP | 1 348 384 | 10/2003 |
| EP | 1 384 456 A2 | 1/2004 |
| EP | 1 405 603 A2 | 4/2004 |
| EP | 1 406 203 | 4/2004 |
| EP | 1 435 223 A1 | 7/2004 |
| EP | 1 442 715 | 8/2004 |
| EP | 1 459 686 A2 | 9/2004 |
| EP | 1 532 946 A2 | 5/2005 |
| EP | 1 563 795 | 8/2005 |
| FR | 2 828 397 | 2/2003 |
| GB | 2 224 937 | 5/1990 |
| GB | 2 397 769 A | 8/2004 |
| JP | 2002-304439 | 10/2002 |
| WO | WO 86/05384 | 9/1986 |
| WO | WO 89/09570 | 10/1989 |
| WO | WO 94/17733 | 8/1994 |
| WO | WO 95/15714 | 6/1995 |
| WO | WO 96/35387 | 11/1996 |
| WO | WO 97/16129 | 5/1997 |
| WO | WO 97/23172 | 7/1997 |
| WO | WO 97/29683 | 8/1997 |
| WO | WO 98/29032 | 7/1998 |
| WO | WO 98/46169 | 10/1998 |
| WO | WO 99/15097 | 4/1999 |
| WO | WO 99/27860 | 6/1999 |
| WO | WO 99/60939 | 12/1999 |
| WO | WO 99/65380 | 12/1999 |
| WO | WO 00/00093 | 1/2000 |
| WO | WO 00/21442 | 4/2000 |
| WO | WO 00/47103 | 8/2000 |
| WO | WO 00/64367 | 11/2000 |
| WO | WO 01/01845 A2 | 1/2001 |
| WO | WO 01/19271 A2 | 3/2001 |
| WO | WO 01/34050 A2 | 5/2001 |
| WO | WO 01/34050 A3 | 5/2001 |
| WO | WO 01/64124 A1 | 9/2001 |
| WO | WO 01/67979 A1 | 9/2001 |
| WO | WO 01/91647 A1 | 12/2001 |
| WO | WO 01/93770 A1 | 12/2001 |
| WO | WO 02/24096 A1 | 3/2002 |
| WO | WO 02/41794 A1 | 5/2002 |
| WO | WO 02/063236 A1 | 8/2002 |
| WO | WO 02/063236 A3 | 8/2002 |
| WO | WO 02/064042 | 8/2002 |
| WO | WO 02/067783 | 9/2002 |
| WO | WO 02/067784 | 9/2002 |
| WO | WO 02/067800 | 9/2002 |
| WO | WO 02/080824 A1 | 10/2002 |
| WO | WO 03/006107 | 1/2003 |
| WO | WO 03/015642 | 2/2003 |
| WO | WO 03/030787 | 4/2003 |
| WO | WO 03/034213 A2 | 4/2003 |
| WO | WO 03/034933 A1 | 5/2003 |
| WO | WO 03/037192 A1 | 5/2003 |
| WO | WO 03/039377 | 5/2003 |
| WO | WO 03/041566 A2 | 5/2003 |
| WO | WO 03/065931 | 8/2003 |
| WO | WO 03/065949 A2 | 8/2003 |
| WO | WO 03/068090 A1 | 8/2003 |
| WO | WO 03/071969 A1 | 9/2003 |
| WO | WO 03/075740 A2 | 9/2003 |
| WO | WO 03/079940 | 10/2003 |
| WO | WO 03/096870 A2 | 11/2003 |
| WO | WO 2004/001569 A2 | 12/2003 |
| WO | WO 2004/017842 A2 | 3/2004 |
| WO | WO 2004/019792 | 3/2004 |
| WO | WO 2004/029908 A1 | 4/2004 |
| WO | WO 2004/030556 A2 | 4/2004 |
| WO | WO 2004/030559 A1 | 4/2004 |
| WO | WO 2004/046754 A2 | 6/2004 |
| WO | WO 2004/069036 | 8/2004 |
| WO | WO 2004/070580 | 8/2004 |
| WO | WO 2004/084740 | 10/2004 |
| WO | WO2004084740 A1 | 10/2004 |
| WO | WO 2005/009303 A1 | 2/2005 |
| WO | WO 2005/039430 A2 | 5/2005 |
| WO | WO 2005/041802 A1 | 5/2005 |
| WO | WO 2005/044126 A1 | 5/2005 |
| WO | WO 2005/048851 A1 | 6/2005 |
| WO | WO 2005/053559 A1 | 6/2005 |
| WO | WO 2005/057439 | 6/2005 |
| WO | WO 2005/070312 A1 | 8/2005 |
| WO | WO 2005/070319 A1 | 8/2005 |
| WO | WO 2005/072629 A1 | 8/2005 |
| WO | WO 2005/096982 | 10/2005 |
| WO | WO 2005/104977 | 11/2005 |
| WO | WO 2005/104978 | 11/2005 |
| WO | WO 2006/044367 A1 | 4/2006 |
| WO | WO 2006/060631 A1 | 6/2006 |
| WO | WO 2006/078236 A1 | 7/2006 |
| WO | WO 2008/021494 | 2/2008 |

OTHER PUBLICATIONS

Smith & Nephew Total Hip Replacement Surgery, HipReplacementInfo.com, 3 pages, Nov. 08, 2005 http://www/hipreplacementinfo.com/hip-total-replacement.htm.
Smith & Nephew Brochure, Design Features, "Opera" pp. 4-15 (1999).
Corinth Surgeon Performs Revolutionary Hip Replacement, Mississippi Medical News, pp. 1-2 (Nov. 17, 2005) http://host1.bondware.com/-mississippi/news.php?viewStory=347.
Dario, et al., 'Smart Surgical Tools and Augmenting Devices,' IEEE Trans. Rob. Autom., 19(5):782-792 (2003).
Fernandez-Lozano, et al., 'Human-machine interface evaluation in a computer assisted surgical system,' Proc. IEEE Int. Conf. Rob. Autom., 2004:231-236 (2004).
Martelli, et al., 'Criteria of interface evaluation for computer assisted surgery systems,' Int. J. Med. Informatics, 72:35-45 (2003).
Visarius, et al., 'Man-machine interfaces in computer assisted surgery,' Computer Aided Surgery, pp. 102-107 (2004).

National Institute of Arthritis and Musculoskeletal and Skin Diseases (NIAMS), "Questions & Answers and . . . Knee Problems", 36 pp. (May 2001).

AO Development Institute "MEPUC Motorized Exact Positioning Unit for C-arm," one page (Jul. 7, 2003) http://www.ao-asif.ch/development/adi/examples/mepuc.shtml.

AO Development Institute "MEPUC Motorized Exact Positioning Unit . . . " one page (Mar. 26, 2003) http://www/ao-asif.ch/development/adi/examples/mepuc.shtml.

Barnes, et al., "Unicompartmental Knee Arthroplasty," *Bombay Hospital Journal*, Issue Special, pp. 1-5, www.bhj.org/journal/1996/3803_july/special_486.htm.

Bonecraft Carnegie Mellon Computer-Aided Bone Deformity Correction Brochure, pp. 1-5, undated.

Bonutti, "Total Joint Replacement Surgery in the 21$^{st}$ Century—New 'Limited-Incision' Total Knee Replacement Offers Important Advantages," 01 page, undated.

Bonutti, et al., "Minimal Incision Total Knee Arthroplasty Using the Suspended Leg Technique," *Orthopedics*, (published Sep. 2003), 6 pages http://www.orthobluejournal.com/0903/9tips.asp.

BrainLAB Brochure entitled "Ortho . . . Your Partner for the Future" pp. 1-28 (2002).

Croitoru, et al., "Fixation-Based Surgery: A New Technique for Distal Radius Osteotomy," *Clinical Paper, Computer Aided Surgery* 2001, 160-169, vol. 6 (2001).

Delp, et al., "Computer-Assisted Knee Replacement," *Clinical Orthopaedics and Related Research*, 354:49-56 (1998).

Deluzio, et al., "Static alignment and the adduction moment in unicompartmental arthroplasty patients," Presented at NACOB 98: North American Congress on Biomechanics, University of Waterloo, Ontario, Canada, Aug. 14-18, 1998.

DiGioia, et al., "Computer Assisted Orthopedic Surgery," *Clinical Orthopaedics and Related Research*, Sep. 1998, vol. 354, pp. 8-16.

Ellis, et al., "A Surgical Planning and Guidance System for High Tibial Osteotomy," *Journal of Computer-Assisted Surgery*, 4(5):264-274 (1999).

Foley, et al., "Percutaneous pedicle screw fixation of the lumbar spine," *Neurosurg. Focus*, vol. 10(4), pp. 1-8 (2001).

Glossop, http:/www/traxta.com/papers/cua/model.html, 8 pages (Feb. 6, 2002).

iON™ Smith & Nephew Orthopaedics Brochure entitled "You'll Never Look At Your Patients The Same Way Again." 10 pages (Jan. 2001).

Iyun, et al., "Planning and Performing the Ilizarov Method with the Taylor Spatial Frame," Abstract, at 2$^{nd}$ Annual Meeting of International Society for Computer Assisted Orthopaedic Surgery, Jun. 21, 2002, pp. 145-147.

Kanade, et al., "Image-Based Computer Assisted Orthopedic Surgery System," Bonecraft, Inc., 12 pages, Apr. 30, 2001.

Kiefer, et al., "Computer Aided Knee Arthroplasty Versus Conventional Technique—First Results," First Annual Meeting of the International Society for Computer Assisted Orthopedic Surgery, Davos, Switzerland, Feb. 8-10, 2001.

Kunz, et al., "Development and Verification of a Non-CT Based Total Knee Arthroplasty System for the LCS Prosthesis," First Annual Meeting of the International Society for Computer Assisted Orthopedic Surgery, Davos, Switzerland, Feb. 8-10, 2001.

Medtronic Surgical Navigation Technologies "Overview Image-Guided Surgery An Advanced Solution to Traditional Surgery," two pages, undated.

Medtronic Surgical Navigation Technologies SNT Vertek photograph, one page, undated.

Medtronic Surgical Navigation Technologies System Components photograph Vertek Platform, one page, undated.

Munoz, et al., "Computer Assisted Planning of Hig Tibial Osteotomy for the Treatment of Knee Osteoarthritis," http://www.utc.fr/esb/esb09/abs_htm/570.html (Feb. 21, 2002) (three pages).

Patent Abstracts of Japan, vol. 2002, No. 05, May 3, 2002 & JP 2002 017740 A (Ochi Takahiro; Yonenobu Sakuo: MMT:KK) Jan. 22, 2002 Abstract.

Picard, et al., "Kneenav.TKR: Concept and Clinical Application," Computer Assisted Orthopedic Surgery USA 2000 Meeting, Pittsburgh, PA., Jun. 15-17, 2000.

Saragaglia, et al., "Computer Assisted Total Knee Arthroplasty: Comparison with a Conventional Procedure. Results of a 50 Cases Prospective Randomized Study," First Annual Meeting of the International Society for Computer Assisted Orthopedic Surgery, Davos, Switzerland, Feb. 8-10, 2001.

Simon, et al., "The Fundamentals of Virtual Fluoroscopy," Medtronic Surgical Navigation Technologies, Medtronic, pp. 57-66, Computer Assisted Orthopedic Surgery USA 2000 Meeting, Pittsburgh, PA, Jun. 15-17, 2000.

Smith & Nephew—Orthopaedics—CAS—Knees Computer Assisted Total Knee Replacement Surgery, 02 pages (Oct. 13, 2004) http://ortho.smith-nephew.com/us/Standard.asp?NodeID=3396.

Smith & Nephew—Orthopaedics—TriGen Flexible Reamer System http://www.smithnephew.com/US/Standard.asp?NodeID=2998, 02 pages (Jan. 21, 2003).

Smith & Nephew—Orthopaedics—TriGen Reducer http://www.smithnephew.com/US/Standard.asp?NodeID=2996, one page (Jan. 21, 2003).

Smith & Nephew Brochure entitled "Surgical Technique Mini Incision Hip Posterior Approach," 20 pages (Mar. 2003).

Smith & Nephew First Choice in Orthopaedics Brochure Entitled "Achieve Computer Assisted Surgery Trauma Applications The Orbiter Base Station & Satellite Surgical Platform," 18 pages, undated.

Smith & Nephew Genesis II "Total Knee System Primary Surgical Technique," Brochure, pp. 1-36 (Mar. 2001).

Smith & Nephew Orthopaedic product bulletin, 01 page.

Smith & Nephew Richards Genesis® "Total Knee System Primary Surgical Technique Anterior Referencing Instrumentation," pp. 59 (Dec. 1993).

Smith & Nephew Richards Genesis® Total Knee System, "Revision Posterior Referencing Instrumentaion Surgical Technique," Brochure, pp. 1-51 (Dec. 1993).

Stryker Navigation System brochure entitled ". . . best alignment for gap kinematics," 6 pages (2001).

Sugano, et al., "Medical Robotics and Computer-Assisted Surgery in the Surgical Treatment of Patients and Rheumatic Diseases," *Cutting Edge Reports*, http://www/rheuma21st.com/archives/cutting_edge_Robotics_Japan.html (Apr. 27, 2000).

Suhm, et al., "Adapting the C-Arm Fluoroscope for Image Guided Orthopaedic Surgery," *CAOS*, pp. 212-214 (2002).

Tenbusch, et al., "First Results Using the Robodoc® System for Total Knee Replacement," First Annual Meeting of the International Society for Computer Assisted Orthopedic Surgrey, Davos, Switzerland, Feb. 8-10, 2001.

Tricon Total Knee System, "Tricon-M® with Pro-Fit™ Surgical Procedures," Richards Brochure, pp. 1-29, undated.

Valstar, et al., "Towards computer-assisted surgery in should joint replacement," *ISPRS Journal of Photogrammetry & Remote Sensing*, 56:326-337 (2002).

DePuy, a Johnson & Johnson Company, Brochure entitled 'S-ROM Modular Hip System Minimally Invasive Calcar Miller Surgical Technique,' 12 pages (2004).

Hafez, et al., 'Computer-assisted Total Knee Arthroplasty Using Patient-specific Templating,' *Clinical Orthopaedics and Related Research*, No. 444, pp. 184-192 (2006).

METHODS AND APPARATUSES FOR PROVIDING A REFERENCE ARRAY INPUT DEVICE

RELATED APPLICATION

This application relates to and claims the benefit on U.S. Provisional Application No. 60/557,872, filed Mar. 31, 2004 and entitled "Reference Array Based User Input Device," the entire contents of which are hereby expressly incorporated by this reference.

TECHNICAL FIELD

The invention relates to computer-aided surgery, and more particularly relates to methods and apparatuses for providing a reference array input device for use in a computer-aided surgery.

BACKGROUND

Many surgical procedures require a wide array of instrumentation and other surgical items. Necessary items may include, but are not limited to: sleeves to serve as entry tools, working channels, drill guides and tissue protectors; scalpels; entry awls; guide pins; reamers; reducers; distractors; guide rods; endoscopes; arthroscopes; saws; drills; screwdrivers; awls; taps; osteotomes and wrenches. In many surgical procedures, including orthopedic procedures, it may be desirable to associate some or all of these items with a guide and/or handle incorporating a surgical reference, allowing the instrument to be used with a computer-aided surgical navigation system.

Several manufacturers currently produce computer-aided surgical navigation systems. The TREON™ and ION™ systems with FLUORONAV™ software manufactured by Medtronic Surgical Navigation Technologies, Inc. are examples of such systems. The BrainLAB VECTORVISION™ system is another example of such a surgical navigation system. Systems and processes for accomplishing computer-aided surgery are also disclosed in U.S. Ser. No. 10/084,012, filed Feb. 27, 2002 and entitled "Total Knee Arthroplasty Systems and Processes"; U.S. Ser. No. 10/084,278, filed Feb. 27, 2002 and entitled "Surgical Navigation Systems and Processes for Unicompartmental Knee Arthroplasty"; U.S. Ser. No. 10/084,291, filed Feb. 27, 2002 and entitled "Surgical Navigation Systems and Processes for High Tibial Osteotomy"; International Application No. US02/05955, filed Feb. 27, 2002 and entitled "Total Knee Arthroplasty Systems and Processes"; International Application No. US02/05956, filed Feb. 27, 2002 and entitled "Surgical Navigation Systems and Processes for Unicompartmental Knee Arthroplasty"; International Application No. US02/05783 entitled "Surgical Navigation Systems and Processes for High Tibial Osteotomy"; U.S. Ser. No. 10/364,859, filed Feb. 11, 2003 and entitled "Image Guided Fracture Reduction," which claims priority to U.S. Ser. No. 60/355,886, filed Feb. 11, 2002 and entitled "Image Guided Fracture Reduction"; U.S. Ser. No. 60/271,818, filed Feb. 27, 2001 and entitled "Image Guided System for Arthroplasty"; and U.S. Ser. No. 10/229,372, filed Aug. 27, 2002 and entitled "Image Computer Assisted Knee Arthroplasty", the entire contents of each of which are incorporated herein by reference as are all documents incorporated by reference therein.

These systems and processes use position and/or orientation tracking sensors such as infrared sensors acting stereoscopically or other sensors acting in conjunction with surgical references to track positions of body parts, surgery-related items such as implements, instrumentation, trial prosthetics, prosthetic components, and virtual constructs or references such as rotational axes which have been calculated and stored based on designation of bone landmarks. Processing capability such as any desired form of computer functionality, whether standalone, networked, or otherwise, takes into account the position and orientation information as to various items in the position sensing field (which may correspond generally or specifically to all or portions or more than all of the surgical field) based on sensed position and orientation of their associated surgical references, or based on stored position and/or orientation information. The processing functionality correlates this position and orientation information for each object with stored information, such as a computerized fluoroscopic imaged field, a wire frame data file for rendering a representation of an instrument component, trial prosthesis or actual prosthesis, or a computer generated file relating to a rotational axis or other virtual construct or reference. The processing functionality then displays position and orientation of these objects on a rendering functionality, such as a screen, monitor, user interface, or otherwise. Thus, these systems or processes, by sensing the position of surgical references, can display or otherwise output useful data relating to predicted or actual position and orientation of surgical instruments, body parts, surgically related items, implants, and virtual constructs for use in navigation, assessment, and otherwise performing surgery or other operations.

Some of the surgical references used in these systems may emit or reflect infrared light that is then detected by an infrared camera. The references may be sensed actively or passively by infrared, visual, sound, magnetic, electromagnetic, x-ray or any other desired technique. An active reference emits energy, and a passive reference merely reflects energy. Some surgical references may have markers or fiducials that are traced by an infrared sensor to determine the position and orientation of the reference and thus the position and orientation of the associated instrument, item, implant component or other object to which the reference is attached.

In addition to surgical references with fixed fiducials, modular fiducials, which may be positioned independent of each other, may be used to reference points in the coordinate system. Modular fiducials may include reflective elements which may be tracked by two, sometimes more, sensors whose output may be processed in concert by associated processing functionality to geometrically calculate the position and orientation of the item to which the modular fiducial is attached. Like fixed fiducial surgical references, modular fiducials and the sensors need not be confined to the infrared spectrum—any electromagnetic, electrostatic, light, sound, radio frequency or other desired technique may be used. Similarly, modular fiducials may "actively" transmit reference information to a tracking system, as opposed to "passively" reflecting infrared or other forms of energy.

Surgical references useable with the above-identified navigation systems may be secured to any desired structure, including the above-mentioned surgical instruments and other items. The surgical references may be secured directly to the instrument or item to be referenced. However, in many instances it will not be practical or desirable to secure the surgical references to the instrument or other item. Rather, in many circumstances it will be preferred to secure the surgical references to a handle and/or a guide adapted to receive the instrument or other item. For example, drill bits and other rotating instruments cannot be tracked by securing the surgical reference directly to the rotating instrument because the reference would rotate along with the instrument. Rather, a preferred method for tracking a rotating instrument is to associate the surgical reference with the instrument or item's guide or handle.

Various arrangements and combinations of fiducials or markers, such as navigational arrays, have been implemented for use with computer-aided surgical navigation systems. Conventional navigational arrays typically include coplanar markers, wherein all of the markers are in a single plane. Use of such navigational arrays can be affected by "line of sight" problems. That is, when the angle between the plane of the array and the camera becomes acute, a marker may be obscured by other markers that are coplanar with it, resulting in limited visibility of the array. When all of the markers in the array cannot be seen in an image, locating the exact position of the marker relative to a patient's body can be difficult. When line of sight problems occur during a computer-aided surgical procedure, the position of the surgical instrument associated with the navigational array or the position of the navigational array itself must be realigned or repositioned, increasing the time and effort associated with the surgical procedure.

In some of these systems, a user or surgeon can input data to the processing functionality via a keyboard, mouse, tablets, or touch screen. However, these types of input devices can be difficult to sterilize prior to or during a surgical procedure. Operation of these types of devices while performing a surgical procedure can also be cumbersome and increase the time needed to perform the procedure. Other systems utilize input devices on a probe or other surgical instrument to input data to the processing functionality. However, these types of systems can be expensive and complex to operate.

SUMMARY

Some or all of the above needs are addressed by aspects and embodiments of the present invention. Various aspects and embodiments of the present invention include reference array input devices adapted to be sensed by a computer-aided surgical navigation system. Such reference array input devices can facilitate selection of one or more instructions or commands associated with a computer-aided surgical navigation system. Such reference array input devices can also be adapted for mounting to a wide variety of surgical instruments and other items. The reference array input devices can allow particular positions and orientations of the reference array input devices to be sensed by a computer-aided surgical navigation system. For instance, reference array input devices according to certain embodiments of the present invention may be used to locate particular positions and orientations of the reference array input devices with respect to a patient's body for performance of surgical procedures, such as installation of an implant. Additionally, reference array input devices according to certain embodiments of the present invention may allow particular positions and orientations of surgical instruments and other items associated with the reference array input devices to be registered in and tracked by a computer-aided surgical navigation system. Such systems may track the position and orientation of the surgical item by tracking the position and orientation of the surgical reference associated with the reference array input devices.

Reference array input devices according to certain aspects and embodiments of the present invention may include fiducial members, indication detectors, and a mount. In one embodiment, a plurality of fiducial members is adapted to be sensed by at least two sensors associated with a computer-aided surgical navigation system in order to determine position and orientation of the reference array input device by the system. A plurality of indication detectors is adapted to facilitate selection of corresponding instructions associated with the computer-aided surgical navigation system. A mount can be adapted to support the reference array input device adjacent to an object.

In at least one embodiment, a reference array input device can be associated with an object such as a surgical instrument or other surgically-related device.

Methods according to certain aspects and embodiments of the present invention may include a method for performing a surgical procedure using a reference array input device and a computer-aided surgical navigation system. In one embodiment, a method can include mounting a reference array input device adjacent to an object or surgical instrument. The reference array input device in this embodiment can include a plurality of fiducial members adapted to be sensed by at least two sensors associated with the computer-aided surgical navigation system in order to determine position and orientation of the reference array input device by the system. Further, the reference array input device can include a plurality of indication detectors adapted to facilitate selection of a corresponding instruction associated with the computer-aided surgical navigation system. The reference array input device can also include a mount adapted to support the reference array input device adjacent to an object or surgical instrument. The method can also include sensing a portion of at least three of the fiducial members by a computer-aided surgical navigation system, and determining a position associated with the object or surgical instrument based in part on sensing the portions of the at least three of the fiducial members. The method further includes selecting at least one of the indication detectors, whereby a corresponding instruction can be received by the computer-aided surgical navigation system.

Methods in accordance with embodiments of the invention can include a method for locating a position of a joint replacement prosthesis using a computer-aided surgical navigation system. The method can include providing a reference array input device. The reference array input device in this embodiment can include a plurality of fiducial members adapted to be sensed by at least two sensors associated with the computer-aided surgical navigation system in order to determine position and orientation of the reference array input device by the system. Further, the reference array input device can include a plurality of indicator detectors adapted to facilitate selection of a corresponding instruction associated with the computer-aided surgical navigation system. The reference array input device can also include a mount adapted to support the reference array input device adjacent to a joint replacement prosthesis. The method can also include mounting the reference array input device adjacent to a joint replacement prosthesis, and sensing a portion of at least three of the fiducial members by a computer-aided surgical navigation system. Furthermore, the method can include determining a position associated with the joint replacement prosthesis based in part on sensing the portions of the at least three of the fiducial members, and selecting at least one of the indicator detectors, whereby a corresponding instruction can be received by the computer-aided surgical navigation system. The method also includes mounting the joint replacement prosthesis to another corresponding joint replacement prosthesis for a joint replacement.

DETAILED DESCRIPTION

Figure 1:
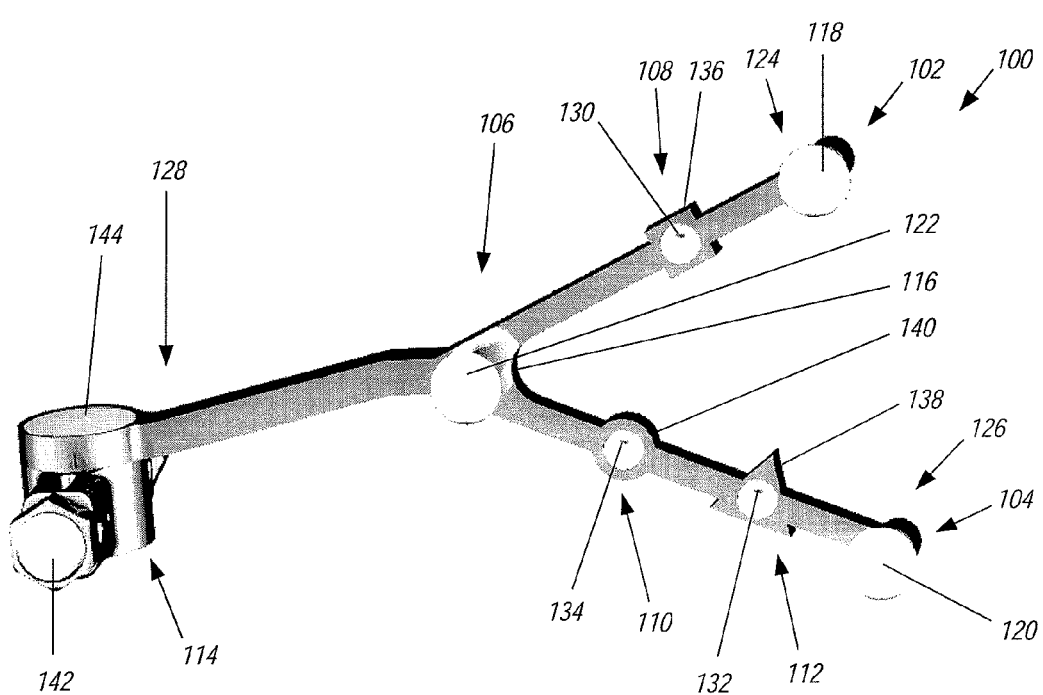
FIG. 1 shows a reference array input device according to an embodiment of the present invention in perspective view.

FIG. 1 shows a reference array input device 100 according to a first embodiment of the present invention. A reference array input device 100 can be used to define the position and orientation of various surgical instruments, orthopedic devices, or other surgical items. The reference array input device 100 can allow surgical instruments, orthopedic devices, or other surgical items to be tracked by a computer-aided surgical navigation system, such as the system 200 shown in FIG. 2. The reference array input device 100 can also provide one or more input devices adapted to provide one or more corresponding instructions to a computer-aided surgical navigation system, such as 200 in FIG. 2. In some embodiments, a reference array input device 100 can be used to mark exterior or interior portions of an individual or body to be tracked by a computer-aided surgical navigation system, such as 200 in FIG. 2.

The reference array input device 100 shown in FIG. 1 includes at least one fiducial member 102, 104, 106; at least one input device 108, 110, 112; and a mount 114. Each of the fiducial members 102, 104, 106 can be positioned for sensing by at least two sensors associated with a computer-aided surgical navigation system (shown as 200 in FIG. 2) in order to determine position and orientation of the reference array input device 100 by the system 200. A portion of each of the three fiducial members 102, 104, 106 intersects at a common point 116, while respective ends of the fiducial members 102, 104, 106 extend away from the common point 116. In this example, the common point 116 connects at least some or all of the fiducial members 102, 104, 106. Furthermore in the example shown, the common point 116 is "non-segmenting" since the common point does not subdivide or segment all of the fiducial members into sub-portions. In the embodiment shown, each of the three of the fiducial members 102, 104, 106 are arranged to form a flat Y-shaped configuration. In another embodiment, a fourth fiducial member (not shown) can extend from the common point 116, and can be oriented orthogonal to each of the other three fiducial members 102, 104, 106. In other embodiments, each of the fiducial members can be positioned orthogonally to at least one other fiducial member. Greater or fewer numbers of fiducial members can be used with other embodiments of the present invention.

A respective fiducial marker, such as a marker elements 118, 120, 122 can mount adjacent to an opposing end 124, 126, 128 of a fiducial member 102, 104, 106 along a fiducial member, or at the common point 116. Each fiducial marker 118, 120, 122 can include a conventional reflective or radiopaque material, or other material capable of being sensed by a computer-aided surgical navigation system. For example, a fiducial marker 118, 120, 122 can be sensed by a computer-aided surgical navigation system using at least one of the following: infrared, sound, visual, magnetic, electromagnetic, and x-ray.

In one embodiment, a fiducial marker 118, 120, 122 can be integrated with each fiducial member. For example, a fiducial member and fiducial marker can be manufactured as a single, integrated piece, wherein a portion of each fiducial member is capable of being sensed by a computer-aided surgical navigation system.

Figure 2:
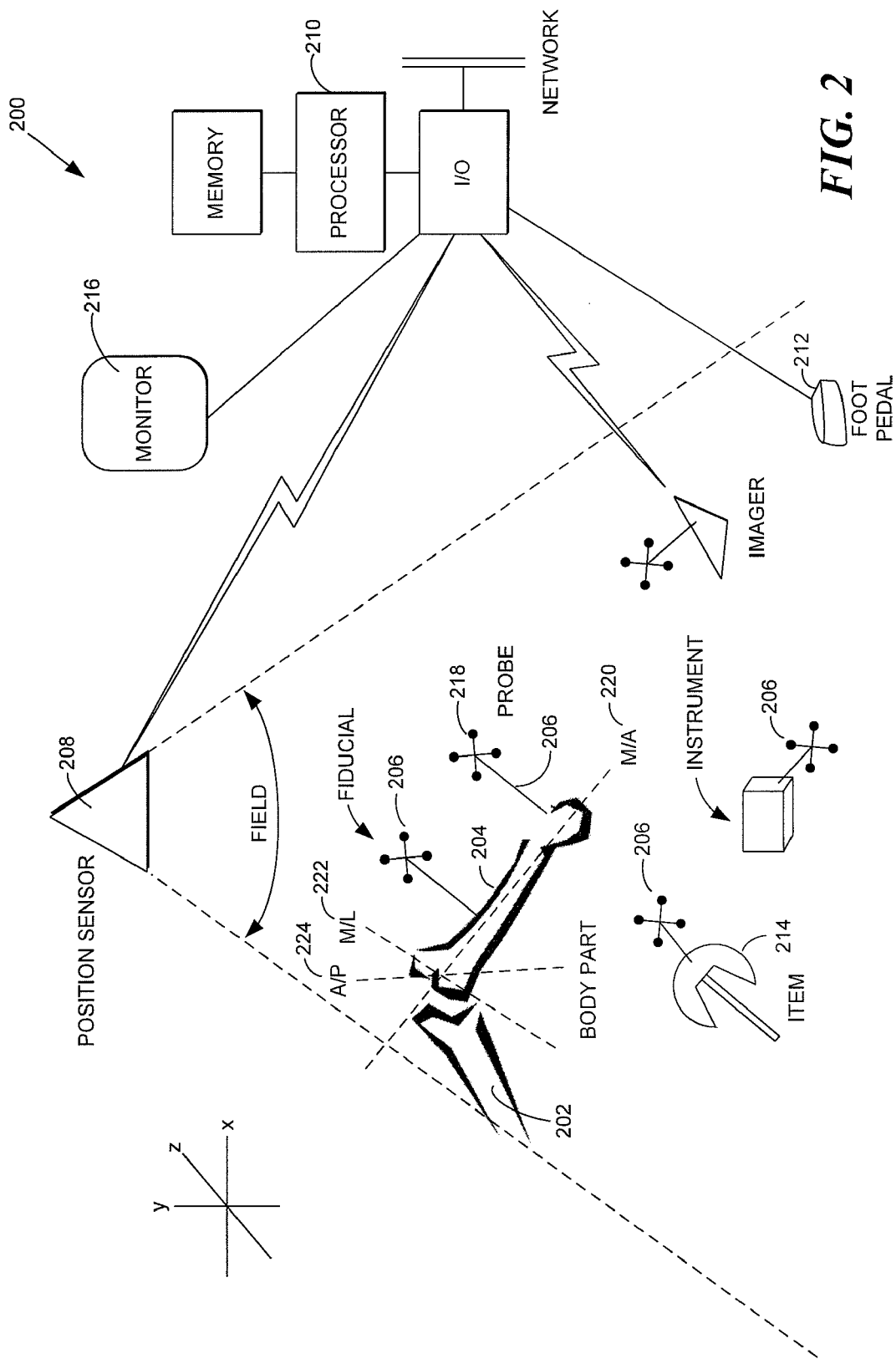
FIG. 2 shows an exemplary environment for use of the reference array input device of FIG. 1 according to an embodiment of the present invention in perspective view.

The embodiment shown in FIG. 1 provides a reference array input device 100 with at least one input device 108, 110, 112 adapted to provide a corresponding instruction to a computer-aided surgical navigation system, such as 200 in FIG. 2. As shown in FIG. 1, an input device 108, 110, 112 can be oriented between the common point 116 and at least one opposing end 124, 126, 128. Each input device 108, 110, 112 can include a respective indication detector 130, 132, 134, and a respective identification indicator 136, 138, 140. Fewer or greater numbers of input devices 108, 110, 112, indication detectors 130, 132, 134, and identification indicators 136, 138, 140 can be used in accordance with embodiments of the present invention. In the embodiment shown, more than one input device, indication detector and/or identification indicator can be oriented between the common point 116 and a single opposing end, such as 126. In another embodiment, multiple input devices, indication detectors and/or identification indicators can be incorporated into a single component oriented between the common point 116 and a single opposing end. In yet another embodiment, one or more input devices, indication detectors and/or identification indicators can be incorporated at the common point 116 and/or opposing end. In those embodiments without a common point 116, one or more input devices, indication detectors and/or identification indicators can be utilized with a reference array input device 100 with at least one fiducial member such as 102, and a mount, such as 114.

In the example shown in FIG. 1, each indication detector 130, 132, 134 can be a metallic cone-shaped recess positioned adjacent to a respective identification indicator 136, 138, 140, such as a unique, geometrically shaped piece mounted to a portion of the reference array input device 100. Each indication detector 130, 132, 134 can be adapted to receive, or otherwise detect, a user input for selecting a particular, predefined instruction for a computer-aided surgical navigation system, such as 200 in FIG. 2. Each respective identification indicator 136, 138, 140 can correspond to a respective predefined instruction for a computer-aided surgical navigation system, such as 200 in FIG. 2.

In one embodiment, a user using a surgical instrument, such as a probe 218 in FIG. 2, associated with a computer-aided surgical navigation system 200 can move the instrument or probe 218 adjacent to, or otherwise make direct contact with, an indication detector, such as 130. The adjacent movement, or direct contact with, an indication detector 130 can be detected, and a corresponding signal indicating the movement or contact can be generated and transmitted to the computer-aided surgical navigation system 200. Computing functionality, such as a processor, associated with the computer-aided surgical navigation system 200 can receive the signal associated with the movement or contact with the indication detector 130. The computing functionality, such as 208 in FIG. 2, can associate the signal with a predefined instruction, and can execute, facilitate, or otherwise carry out the instruction as needed. In one example, the predefined instruction can be an input of a particular length or dimension of an orthopedic device to be installed in a body.

In other embodiments, an indication detector can include, but is not limited to, an input button, an input device, a contact device, a sensor device, a detector device, a transmitter device, a receiver device, or an infrared device. In another embodiments, an identification indictor can include, but is not limited to, a triangle, a square, a circle, a star, a polygon, an oval, a unique geometrical shape, a number, a letter, alphanumeric text, a symbol, or a color. In other embodiments, a user input can include, but is not limited to, direct contact with a portion of a surgical instrument, direct contact with a portion of a user input device, movement of a portion of a surgical instrument adjacent to the indication detector, or movement of a portion of a user input device adjacent to the indication detector. An instruction for a computer-aided surgical navigation system can include, but is not limited to, a tab command, a select command, an increment function, a decrement function, a forward function, a backward function, a functional command, a function, an operational command, an operation. The instruction for a computer-aided surgical navigation system can be associated with at least one of the following: a size selection, a shape selection, a numeric selection, an alphanumeric selection, a selection of a range of sizes, a selection of a range of numbers, a material selection, a body component selection, an orthopedic component selection, or a surgical procedure selection.

The particular arrangement for a reference array input device 100 shown in FIG. 1 can be used by a computer-aided surgical navigation system to locate the position and orientation of the reference array input device 100 by defining at least three fiducial markers at all times. Additional fiducial markers or marker elements, and corresponding axial members, can be used to further reduce the sensitivity of the reference array input device 100 to any "line of sight" problems.

The present invention is not limited to the "Y-shaped" orientation of fiducial members and markers shown in FIG. 1, and can include other orientations in accordance with embodiments of the invention. Other embodiments of a navigational array can include fewer or greater numbers of input devices, fiducial members and/or fiducial markers in accordance with embodiments of the invention. Furthermore, other configurations, shapes, and lengths of input devices, fiducial members and/or fiducial markers can exist in accordance with embodiments of the invention. In other embodiments, input devices, fiducial markers and marker elements can have different configurations than those shown in FIG. 1, such as a geometric shape, a sphere, a block, or a plate. Furthermore, in other embodiments, different geometric shapes can be used for each input device, fiducial marker and/or marker element of a reference array input device.

The mount 114 shown can associate the reference array input device 100 with a portion of a patient's body, a surgical instrument, orthopedic device, or surgical item such as a joint replacement prosthesis. In the example shown in FIG. 1, the mount 114 includes a fixator 142 and an array 144. The fixator 142 can mount to one or more pins that have been previously mounted to a portion of a patient's body. The fixator 142 and array 144 can then be connected, jointed, or otherwise mounted to each other, wherein the array 144 can support the other components of the reference array input device 100. In another embodiment, the mount 114 can include a connector, such as a two-pronged connector that can be mounted to a corresponding two-holed connector previously mounted to a portion of a patient's body, a surgical instrument, or item such as a joint replacement prosthesis. Other configurations for a mount in accordance with embodiments of the invention can exist.

In other embodiments, the mount 114 can be any suitable structure for associating the reference array input device 100 with a portion of a patient's body, a surgical instrument, orthopedic device, or item. For example, a mount 114 can include, but is not limited to, a threaded device, a mechanical-type connecting device, a magnetic-type connecting device, an electro-mechanical or electro-magnetic type connecting device, an adhesive-type connecting device, or any other suitable connecting device adapted to associate the reference array input device 100 with a portion of a patient's body, a surgical instrument, orthopedic device, or item.

In one embodiment, a mount can be formed integrally with a surgical instrument, orthopedic device, or item such as a joint replacement prosthesis, wherein the reference array input device and the surgical instrument, orthopedic device, or item can be manufactured as a single piece.

FIG. 2 is a schematic view showing an environment for using a reference array input device according to the present invention in a surgery on a knee, in this case a knee arthroplasty. A reference array input device according to the present invention can be used to track particular locations associated with various body parts such as tibia 202 and femur 204 to which reference arrays of the sort described above in FIG. 1 may be implanted, attached, or otherwise associated physically, virtually, or otherwise. A reference array input device according to the present invention can also be used to receive a user input and provide one or more corresponding instructions to a computer-aided surgical navigation system, such as 200 in FIG. 2. As shown and described in the embodiment shown in FIG. 1, a reference array input device can include fiducial markers, such as marker elements, capable of being sensed by a computer-aided surgical navigation system. The reference array input device 100 shown in FIG. 1 can also include input devices, such as cone-shaped recesses, capable of receiving or otherwise transmitting a user input to a computer-aided surgical navigation system.

In the example shown in FIG. 2, a position sensor 208 can sense, store, process and/or output data relating to position and orientation of at least one reference array input device 206, and thus components such as 202 and 204 to which they are attached or otherwise associated. The position sensor 208, as mentioned above, may be any sort of sensor functionality for sensing position and orientation of reference array input devices 206, and therefore, items with which they are associated, according to whatever desired electrical, magnetic, electromagnetic, sound, physical, radio frequency, or other active or passive technique. In one embodiment, position sensor 208 is a pair of infrared sensors disposed on the order of a meter, sometimes more, sometimes less, apart and whose output can be processed in concert to provide position and orientation information regarding reference array input devices 206.

Also shown in the example of FIG. 2, computing functionality 210 can communicate with, and receive at least one user input from a reference array input device 206. The computing functionality 210 include processing functionality, memory functionality, input/output functionality whether on a standalone or distributed basis, via any desired standard, architecture, interface and/or network topology. In one embodiment, computing functionality 210 can be connected to a monitor 216 on which graphics and data may be presented to the surgeon during surgery. The monitor 216 preferably has a user interface adapted to receive a user input from the reference array input device 206. The user interface can also permit the surgeon to point and click on the monitor 216 for tactile screen input in addition to or instead of, if desired, keyboard and mouse conventional interfaces. Additionally, a foot pedal 212 or other convenient interface may be coupled to the computing functionality 210 as can any other wireless or wireline interface to allow the surgeon, nurse or other desired user to control or direct the computing functionality 210 in order to, among other things, capture position/orientation information when certain components are oriented or aligned properly. Items 214 such as trial components, instrumentation components may be tracked in position and orientation relative to body parts 202 and 204 using one or more reference array input devices 206.

Computing functionality 210 can process, store and output on monitor 214 and otherwise various forms of data which correspond in whole or part to body parts 202 and 204 and other components for item 214. For example, body parts 202 and 204 can be shown in cross-section or at least various internal aspects of them such as bone canals and surface structure can be shown using fluoroscopic images. These images can be obtained using a C-arm attached to a reference array input device 206. The body parts, for example, tibia 202 and femur 204, can also have reference array input devices 206 attached. When fluoroscopy images are obtained using the C-arm with a reference array input device 206, a position/orientation sensor 208 "sees" and tracks the position of the fluoroscopy head as well as the positions and orientations of the tibia 202 and femur 204. The computing functionality 210 stores the fluoroscopic images with this position/orientation information, thus correlating position and orientation of the fluoroscopic image relative to the relevant body part or parts. Thus, when the tibia 202 and corresponding reference array input device 206 move, the computing functionality 210 automatically and correspondingly senses the new position of tibia 202 in space and can correspondingly move implements, instruments, references, trials and/or implants on the monitor 216 relative to the image of tibia 202. Similarly, the image of the body part can be moved, both the body part and such items may be moved, or the on screen image otherwise presented to suit the preferences of the surgeon or others and carry out the imaging that is desired. Similarly, when an item 214, such as a stylus, cutting block, reamer, drill, saw, extramedullary rod, intramedullar rod, or any other type of item or instrument, that is being tracked moves, its image moves on monitor 216 so that the monitor shows the item 214 in proper position and orientation on monitor 216 relative to the femur 204. The item 214 can thus appear on the monitor 216 in proper or improper alignment with respect to the mechanical axis and other features of the femur 204, as if the surgeon were able to see into the body in order to navigate and position item 214 properly.

The computer functionality 210 can also store data relating to configuration, size and other properties of items 214 such as joint replacement prostheses, implements, instrumentation, trial components, implant components and other items used in surgery. When those are introduced into the field of position/orientation sensor 208, computer functionality 210 can generate and display overlain or in combination with the fluoroscopic images of the body parts 202 and 204, computer generated images of joint replacement prostheses, implements, instrumentation components, trial components, implant components and other items 214 for navigation, positioning, assessment and other uses.

Computer functionality 210 may also store and output virtual construct data based on the sensed position and orientation of items in the surgical field, such as surgical instruments. For example, monitor 216 can output a resection plane that corresponds to the resection plane defined by a cutting guide whose position and orientation is being tracked by sensors 208. In other embodiments, monitor 216 can output a cutting track based on the sensed position and orientation of a reamer. Other virtual constructs can also be output on monitor 216, and can be displayed with or without the relevant surgical instrument, based on the sensed position and orientation of any surgical instrument or other item in the surgical field to assist the surgeon or other user to plan some or all of the stages of the surgical procedure.

In some preferred embodiments of the present invention, computer functionality 210 can output on monitor 216 the projected position and orientation of an implant component or components based on the sensed position and orientation of one or more surgical instruments associated with one or more navigational arrays 206. For example, the system may track the position and orientation of a cutting block as it is navigated with respect to a portion of a body part that will be resected. Computer functionality 210 may calculate and output on monitor 216 the projected placement of the implant in the body part based on the sensed position and orientation of the cutting block. If the surgeon or other user is dissatisfied with the projected placement of the implant, the surgeon may then reposition the cutting block to evaluate the effect on projected implant position and orientation.

Additionally, computer functionality 210 can track any point in the position/orientation sensor 208 field such as by using a designator or a probe 218. The surgeon, nurse, or other user touches the tip of probe 218 to a point such as a landmark on bone structure and actuates the foot pedal 212 or otherwise instructs the computing functionality 210 to note the landmark position. The position/orientation sensor 208 "sees" the position and orientation of reference array input device 206, "knows" where the tip of probe 218 is relative to that reference array input device 206, and thus calculates and stores, and can display on monitor 216 whenever desired and in whatever form or fashion or color, the point or other position designated by probe 218 when the foot pedal 212 is hit or other command is given. Thus, probe 218 can be used to designate landmarks on bone structure in order to allow the computing functionality 210 to store and track, relative to movement of the reference array input device 206, virtual or logical information such as mechanical axis 220, medial lateral axis 222 and anterior/posterior axis 224 of femur 204, tibia 202 and other body parts in addition to any other virtual or actual construct or reference. An example of a probe 218 can be the surgical instrument shown in FIG. 4.

In one embodiment, a reference array input device 206 can be used to calibrate a computer-aided surgical navigation system 200. Using the position and orientation information associated with the sensing of one or more fiducial markers associated with the reference array input device 206, the computing functionality 210 can also receive additional position and orientation information from one or more indication detectors, such as 130 in FIG. 1, associated with the reference array input device 206. When a user moves a tip of a probe 218 adjacent to, or makes contact with, an indication detector, the adjacent movement or contact generates a signal that can be received by the computing functionality 210. The signal can be correlated with the known position and orientation of the indication detector relative to the previously sensed fiducial markers associated with the reference array input device 206. Additional signals provided by other interactions between the probe 218 and other indication detectors can be further utilized by the computing functionality and correlated with the known positions and orientations of those indication detectors relative to the previously sensed fiducial markers associated with the reference array input device 206.

Furthermore, the computing functionality 210 can receive and process a signal corresponding to a user input from a reference array input device 206. For example, a user using a surgical instrument, such as probe 218, associated with the computing functionality, such as a processor, can move the instrument or probe 218 adjacent to, or otherwise make direct contact with, an indication detector, such as 130, associated with the reference array input device 206. The adjacent movement, or direct contact with, an indication detector 130 can be detected, and a corresponding signal indicating the movement or contact can be generated and transmitted to the computing functionality 210. Computing functionality 210, such as a processor, can receive and process the signal associated with the movement or contact with the indication detector 130. The computing functionality 210 or processor can associate the signal with a predefined instruction, and can execute, facilitate, or otherwise carry out the instruction as needed.

In one example, the computing functionality 210 can provide a graphical user interface on a monitor 216. Each indication detector, such as 130, 132, and 134, and respective identification area, such as 136, 138, 140, of a reference array input device 206 can be associated with a corresponding instruction or command facilitated by the user interface. In this example, a user interface can include instructions or commands, such as a size increment button, a size decrement button, and a select button. Each of these buttons can be associated with a corresponding indication detector and identification indicator. When a user operates a probe 218, and moves the probe 218 adjacent to or makes contact with a particular indication detector, a signal associated with a corresponding instruction can be transmitted to, or received by the computing functionality. For example, a triangular shaped identification indicator and respective indication detector can be associated with a size increment button. Each time a user moves the probe 218 adjacent to or makes contact with the indication detector, the user interface receives a signal corresponding to selecting the size increment button. Each receipt of a signal corresponds to a selection of the size increment button. Similarly, a square shaped identification indicator and respective indication detector can be associated with a size decrement button, and a user selection of the indication detector can indicate a selection of the size decrement button on the user interface. In this example, use of the size increment and size decrement buttons can provide input for a desired length or dimension of an orthopedic device to be installed in a body. Furthermore, a circle shaped identification indicator and respective indication detector can be associated with a select/enter button associated with the user interface. A select/enter button can provide a select command associated with the user interface. A select/enter button can provide a select command or instruction within the user interface to select and enter a particular desired command or instruction in the user interface, for example, selecting and entering a desired size previously designated by either or both of the size increment and size decrement buttons. User selection of the indication detector associated with the circle shaped identification indicator can indicate selection of the select/enter button on the user interface. When the select/enter button is selected via the corresponding indication detector and circle shaped identification indicator, the user can select and enter a particular command or instruction displayed by the user interface, such as a previously designated or desired size.

In at least one embodiment, an identification indicator and respective indication detector can be associated with a tab/focus button associated with the user interface. A tab/focus button can provide a tab/focus command or instruction within the user interface to alternate between other commands or instructions in the user interface, for example, alternating between the size increment and size decrement buttons. User selection of the indication detector associated with the circle shaped identification indicator can indicate selection of the tab/focus button on the user interface. When the tab/focus button is selected via the corresponding indication detector and circle shaped identification indicator, the user can move through a series of commands or instructions displayed by the user interface, and select a desired command or instruction.

In other embodiments, other instructions or commands associated with a user interface can be associated with an indication detector and respective identification indicator.

A reference array input device according to an embodiment of the present invention such as the subject of FIG. 1, can use or operate in conjunction with the so-called FluoroNAV system and software provided by Medtronic Sofamor Danek Technologies. Such systems or aspects of them are disclosed in U.S. Pat. Nos. 5,383,454; 5,871,445; 6,146,390; 6,165,81; 6,235,038 and 6,236,875, and related (under 35 U.S.C. Section 119 and/or 120) patents, which are all incorporated herein by this reference. Any other desired systems can be used as mentioned above for imaging, storage of data, tracking of body parts and items and for other purposes.

The FluoroNav system can require the use of reference frame type fiducials which have three, four, and in some cases, five elements tracked by infrared sensors for position/orientation of the fiducials and thus of the body part, implement, instrumentation, trial component, implant component, or other device or structure being tracked. Such systems can also use at least one probe 218 which the surgeon can use to select, designate, register, or otherwise make known to the system a point or points on the anatomy or other locations by placing the probe as appropriate and signaling or commanding the computer to note the location of, for instance, the tip of the probe. The FluoroNav system can also track position and orientation of a C-arm used to obtain fluoroscopic images of body parts to which fiducials have been attached for capturing and storage of fluoroscopic images keyed to position/orientation information as tracked by the sensors 208. Thus, the monitor 216 can render fluoroscopic images of bones in combination with computer generated images of virtual constructs and references together with implements, instrumentation components, trial components, implant components and other items used in connection with surgery for navigation, resection of bone, assessment and other purposes.

Various embodiments of the invention can be used with point of class-type, registration-type, and other surgical location and preparation techniques and methods. For example, in one prosthetic installation procedure, a surgeon can designate a center of rotation of a patient's femoral head for purposes of establishing the mechanical axis and other relevant constructs relating to the patient's femur according to which prosthetic components can ultimately be positioned. Such center of rotation can be established by articulating the femur within the acetabulum or a prosthesis to capture a number of samples of position and orientation information and thus in turn to allow the computer to calculate the average center of rotation. The center of rotation can be established by using a probe associated with a reference array input device 206, and designating a number of points on the femoral head and thus allowing the computer to calculate the geometrical center or a center which corresponds to the geometry of points collected. Additionally, graphical representations such as controllably sized circles displayed on the monitor can be fitted by the surgeon to the shape of the femoral head on planar images using tactile input on screen to designate the centers according to that graphic, such as are represented by the computer as intersection of axes of the circles. Other techniques for determining, calculating or establishing points or constructs in space, whether or not corresponding to bone structure, can be used in accordance with the present invention.

In another example, a reference array input device 206 according to various embodiments of the invention can be used in designation or registration of items which will be used in surgery. Registration simply means, however it is accomplished, ensuring that the computer knows which body part, item or construct corresponds to which fiducial or fiducials, and how the position and orientation of the body part, item or construct is related to the position and orientation of its corresponding fiducial or a fiducial attached to an impactor or other component which is in turn attached to an item. Such registration or designation can be done before or after registering bone or body parts. In one instance, a technician can designate with a probe an item such as an instrument component to which a reference array input device 206 is attached. A sensor associated with a computer-aided surgical navigational system can "see" the position and orientation of the reference array input device 206 attached to the item and also the position and orientation of another reference array input device attached to the probe whose tip is touching one or more indication detectors of the reference array input device 206. The technician can designate onscreen or otherwise the identification of the item and then activates the foot pedal or otherwise instructs the computer to correlate the data corresponding to such identification, such as data needed to represent a particular cutting block component for a particular knee implant product, with the particularly shaped reference array input device 206 attached to the component. The computer has then stored identification, position and orientation information relating to the navigational array for the component correlated with the data such as configuration and shape data for the item so that upon registration, when the sensor can track the item and reference array input device 206 in the infrared field, the monitor can show the cutting block component moving and turning, and properly positioned and oriented relative to the body part which is also being tracked.

Similarly, the mechanical axis and other axes or constructs of body parts can also be "registered" for tracking by the system. Again, the computer-aided surgical navigational system can employ a fluoroscope to obtain images of the patient's femoral head, knee and ankle, or other body parts. The system can correlate such images with the position and orientation of the C-arm and the patient anatomy in real time as discussed above with the use of one or more reference array input device 206 placed on the body parts before image acquisition and which remain in position during the surgical procedure. Using these images and/or the probe, the surgeon can select and register in the computer the center of the femoral head and ankle in orthogonal views, usually anterior/posterior and lateral, on a touch screen. The surgeon can use the probe to select any desired anatomical landmarks or references at the operative site of the knee or on the skin or surgical draping over the skin, as on the ankle. These points can be registered in three dimensional space by the system and can be tracked relative to the navigational arrays on the patient anatomy which are preferably placed intraoperatively. Although registering points using actual bone structure is one preferred way to establish the axis, a cloud of points approach by which the probe is used to designate multiple points on the surface of the bone structure can be employed, as can moving the body part and tracking movement to establish a center of rotation as discussed above. Once the center of rotation for the femoral head and the condylar component have been registered, the computer can calculate, store, and render, and otherwise use data for, the mechanical axis of the femur.

In one example, a tibial mechanical axis can be established by designating points to determine the centers of the proximal and distal ends of a patient's tibia so that the mechanical axis can be calculated, stored, and subsequently used by the computer. A posterior condylar axis can also determined by designating points or as otherwise desired, as rendered on the computer generated geometric images overlain or displayed in combination with the fluoroscopic images, all of which are keyed to one or more reference array input devices being tracked by sensors associated with the computer-aided surgical navigational system.

The above methods and techniques are provided by way of example only, and other embodiments of the present invention can be used with other surgical location and preparation techniques and methods.

Figure 3:
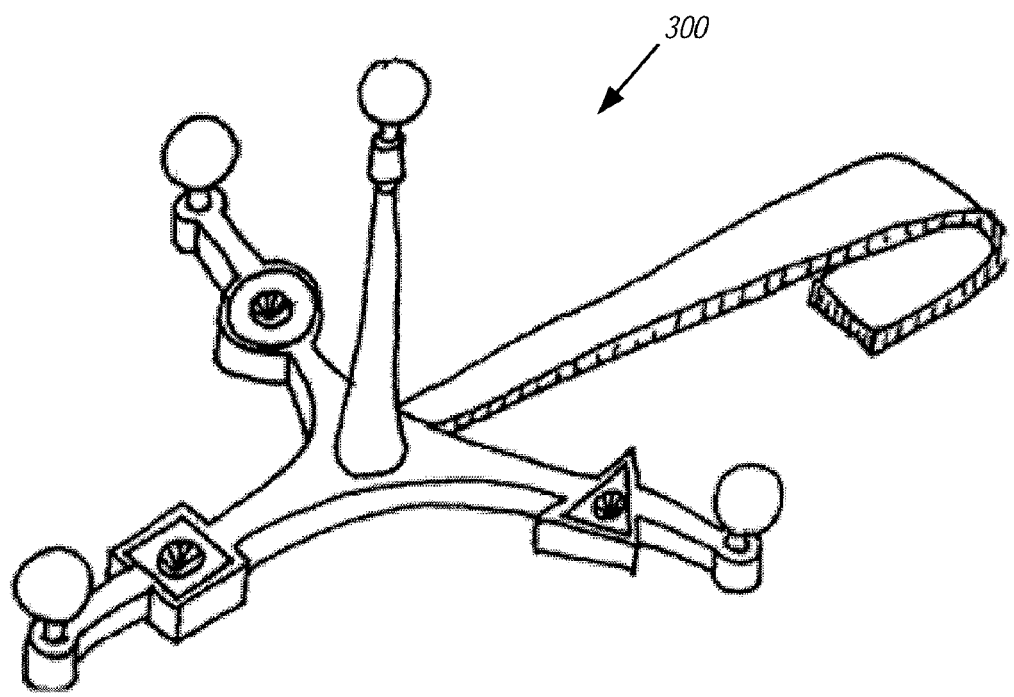
FIG. 3 is a perspective view of a particular embodiment for a reference array input device according to an embodiment of the present invention.

FIG. 3 shows a reference array input device according to another embodiment of the present invention. This example is similar to the device shown in FIG. 1, and is capable of being tracked with a computer-aided surgical navigation system as well as providing a user input for an instruction or command associated with a computer-aided surgical navigation system. The computer-aided surgical navigation system used to track the reference array input device 300 can be similar to the system shown in FIG. 2. In the example shown in FIG. 3, the reference array input device 300 can be rigidly attached to a portion of a patient's body, such as a tibia adjacent to the knee. Attachment of the reference array input device 300 preferably is accomplished using a structure that corresponds with the respective mounts of the reference array input device. Such structures can preferably withstand vibration of surgical saws and other phenomenon which occur during surgery without allowing any substantial movement of the reference array input device 300 relative to the body part being tracked by the computer-aided surgical navigation system.

The fiducial markers or marker elements of the reference array input device 300, 400 shown are capable of being tracked by sensors 208 of the computer-aided surgical navigation system. Thus, when the fiducial markers or marker elements are sensed by the computer-aided surgical navigation system, the system can determine positions associated with the reference array input device 300.

Moreover, indication detectors of the reference array input device 300 shown are capable of transmitting a user input of corresponding instructions or commands associated with the computer-aided surgical navigation system. Thus, when a user moves a tip of a probe or other surgical instrument associated with the computer-aided surgical navigation system adjacent to or makes direct contact with an indication detector, the system can receive a signal associated with a selection of a corresponding user input of a particular instruction or command.

Figure 4:
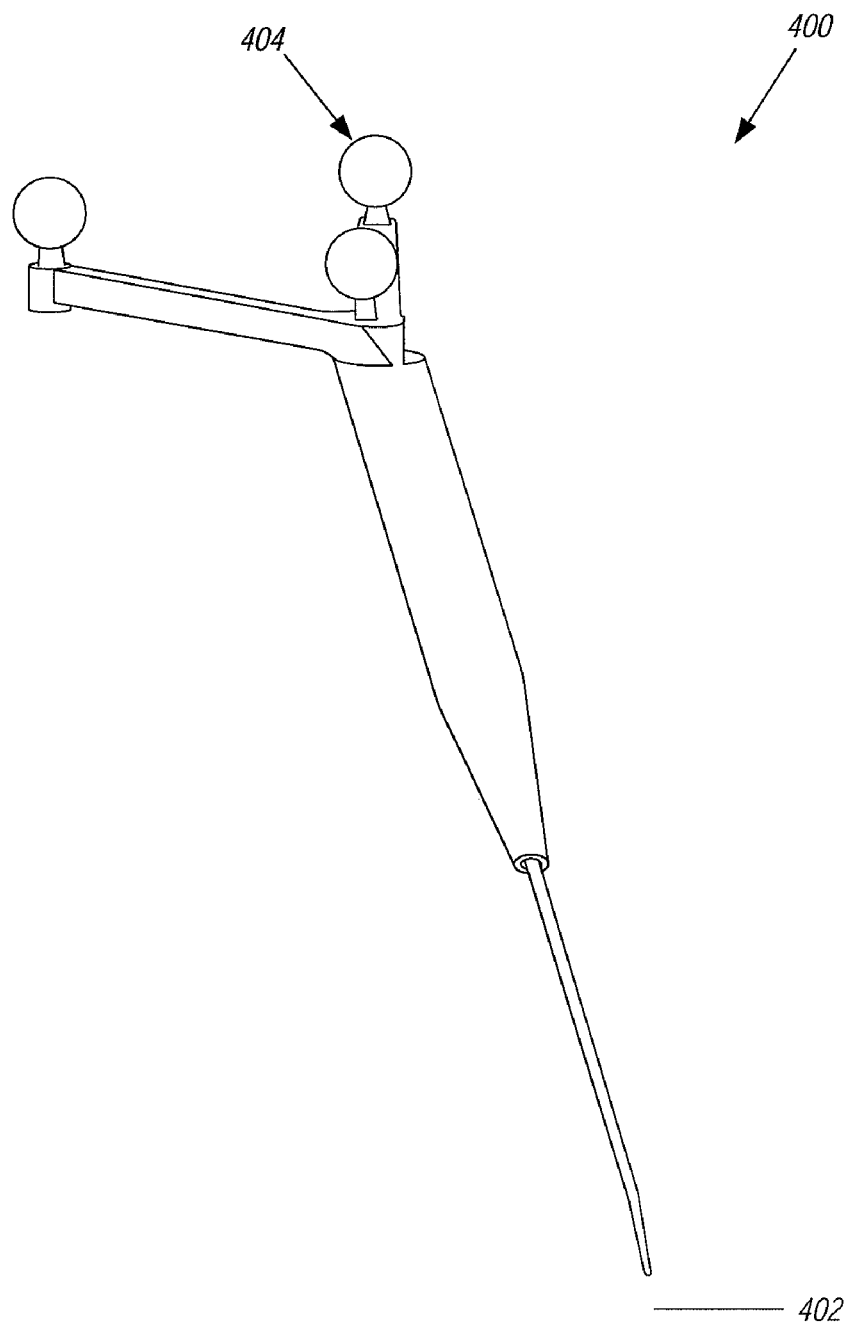
FIG. 4 illustrates an associated surgical instrument for use with a reference array input device according to an embodiment of the present invention.

FIG. 4 illustrates an associated surgical instrument for use with a reference array input device according to another embodiment of the present invention. A surgical instrument for use with a reference array input device can be a probe 400 with a stainless steel tip 402. The tip 402 is adapted to be sensed by, or to detect, an adjacent indication detector associated with a reference array input device, such as indication detector 130 of device 100. Other portions of the probe 400 can be sensed and detected by way of one or more fiducials 404. The interaction between the tip 402 and the indicator area 130 can generate or otherwise cause a signal to be transmitted to a computer-aided surgical navigation system. Thus, when the indicator area 130 is associated with a particular instruction or command associated with the computer-aided surgical navigation system, a user's designation of the indicator area 130 with the tip 402 of the probe 400 can transmit or cause the transmission of a signal associated with user input of the instruction or command. In at least one embodiment, the user will view a user interface associated with a monitor, such as 216 in FIG. 2, for the computer-aided surgical navigation system. The user's selection of an indication detector 130 corresponding to a desired command or instruction can be graphically displayed and reviewed via the user interface.

Figure 5:
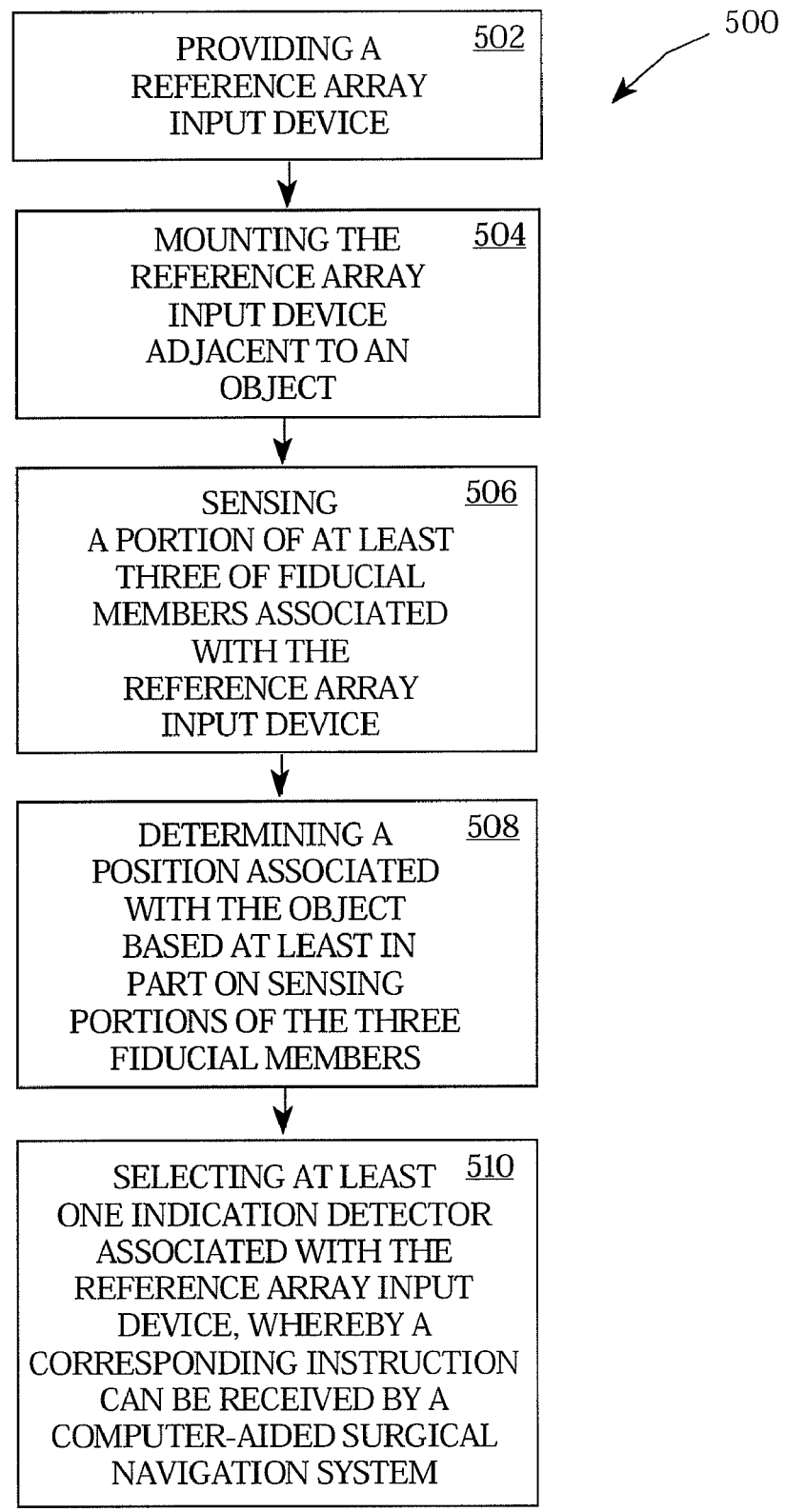
FIG. 5 illustrates a flowchart of a method of use for a reference array input device according to an embodiment of the present invention and a computer-aided surgical navigation system.

FIG. 5 illustrates a flowchart of a method 500 of use for a reference array input device according to an embodiment of the present invention and a computer-aided surgical navigation system.

The method begins at block 502. At block 502, a reference array input device is provided. In the embodiment shown in FIG. 5, the reference array input device can be similar to the reference array input device 100 shown in FIG. 1. The reference array input device in this example can include a plurality of fiducial members, such as a first, second, and third fiducial member, capable of being positioned for sensing by at least two sensors associated with a computer-aided surgical navigation system (shown as 200 in FIG. 2) in order to determine position and orientation of the reference array input device by the system. Each fiducial member can include a portion adapted to be sensed by a computer-aided surgical navigation system, such as a fiducial marker or marker element. Furthermore, the reference array input device can also include a plurality of indication detectors, such as a first, second, and third indication detector, capable of facilitating selection of a corresponding instruction associated with the computer-aided surgical navigation system. Moreover, the reference array input device can include a mount adapted to support the reference array input device adjacent to an object.

Block 502 is followed by block 504, in which a reference array input device is mounted adjacent to an object. The mount associated with the reference array input device can be utilized to support the reference array input device adjacent to an object, such as a portion of a patient's body. An object in this embodiment can include at least one of the following: a patient's bone, a surgical implement, a surgical reference, a surgical trial, an implant, a cutting block, a reamer, a drill, a saw, an extramedullary rod, and an intramedullar rod.

Block 504 is followed by block 506, in which a portion of at least three of the fiducial members is sensed by the computer-aided surgical navigation system. In the embodiment shown in FIG. 5, a computer-aided surgical navigation system similar to that shown in FIG. 2, can be used to sense portions of at least three fiducial members associated with the reference array input device.

Block 506 is followed by block 508, in which a position associated with the object is determined based at least in part on sensing the portions of the at least three fiducial members.

Block 508 is followed by block 510, in which at least one of the indication detectors is selected, whereby a corresponding instruction can be received by the computer-aided surgical navigation system.

The method 500 ends at block 510. Other method elements can exist in accordance with embodiments of the invention.

Figure 6:
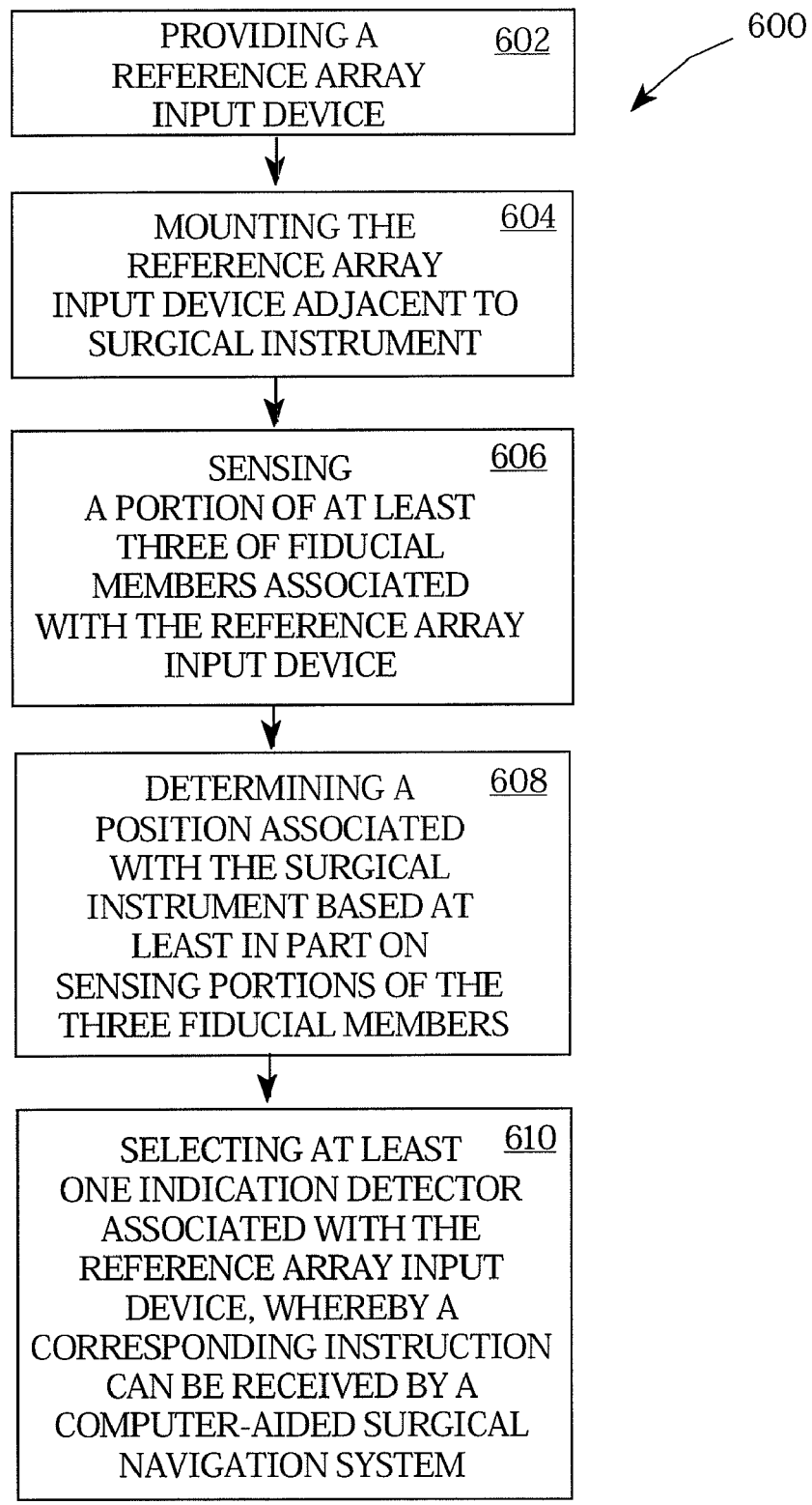
FIG. 6 illustrates a flowchart of a method of use for an apparatus according to an embodiment of the present invention and a computer-aided surgical navigation system.

FIG. 6 illustrates a flowchart of a method 600 of use for an apparatus according to an embodiment of the present invention and a computer-aided surgical navigation system.

The method begins at block 602. At block 602, a reference array input device is provided. In the embodiment shown in FIG. 6, the reference array input device can be similar to the reference array input device 100 shown in FIG. 1. The reference array input device in this example can include a plurality of fiducial members, such as a first, second, third, and fourth fiducial member, capable of being positioned for sensing by at least two sensors associated with a computer-aided surgical navigation system (shown as 200 in FIG. 2) in order to determine position and orientation of the reference array input device by the system. Each fiducial member can include a portion adapted to be sensed by a computer-aided surgical navigation system, such as a fiducial marker or marker element. Furthermore, the reference array input device can also include a plurality of indication detectors, such as a first, second, and third indication detector, capable of facilitating selection of a corresponding instruction associated with the computer-aided surgical navigation system. Moreover, the reference array input device can include a mount adapted to support the reference array input device adjacent to an object.

Block 602 is followed by block 604, in which a reference array input device is mounted adjacent to a surgical instrument. A surgical instrument in this embodiment can include at least one of the following: a surgical implement, a surgical reference, a surgical trial, an implant, a cutting block, a reamer, a drill, a saw, an extramedullary rod, and an intramedullar rod.

Block 604 is followed by block 606, in which a portion of at least three of the fiducial members is sensed by the computer-aided surgical navigation system. In the embodiment shown in FIG. 6, a computer-aided surgical navigation system similar to that shown in FIG. 2, can be used to sense portions of at least three fiducial members associated with the navigational array.

Block 606 is followed by block 608, in which a position associated with the apparatus is determined based at least in part on sensing the portions of the at least three fiducial members.

Block 608 is followed by block 610, in which at least one of the indication detectors is selected, whereby a corresponding instruction is received by the computer-aided surgical navigation system.

The method 600 ends at block 610. Other method elements can exist in accordance with embodiments of the invention.

Figure 7:
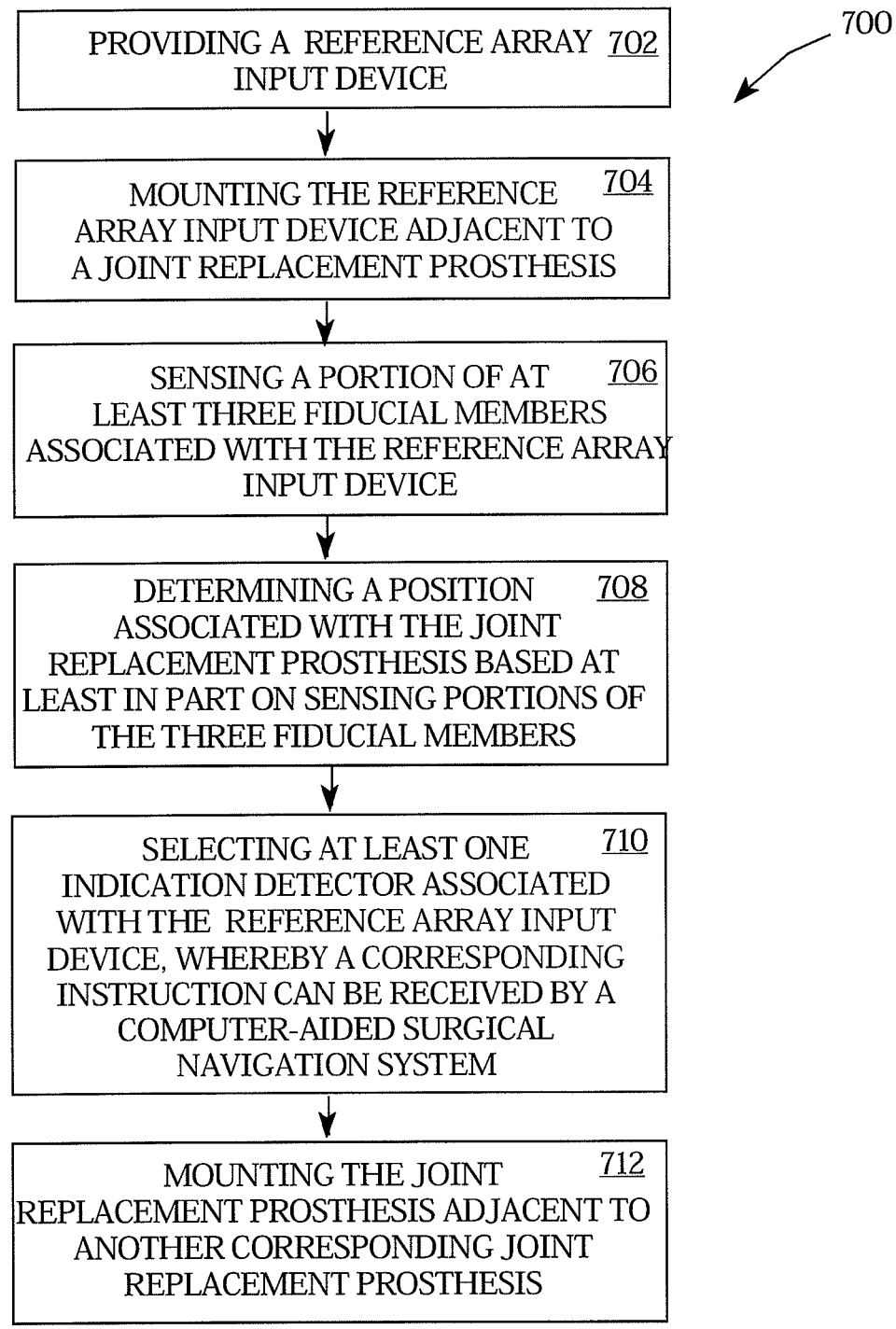
FIG. 7 illustrates a flowchart of a method of use for an apparatus according to an embodiment of the present invention and a computer-aided surgical navigation system.

FIG. 7 illustrates a flowchart of a method 700 of use for a reference array input device according to an embodiment of the present invention and a computer-aided surgical navigation system.

The method begins at block 702. At block 702, a reference array input device is provided. In the embodiment shown in FIG. 7, the reference array input device can be similar to the reference array input device 100 shown in FIG. 1. The reference array input device in this example can include a plurality of fiducial members, such as a first, second, third, and fourth fiducial member, capable of being positioned for sensing by at least two sensors associated with a computer-aided surgical navigation system (shown as 200 in FIG. 2) in order to determine position and orientation of the array by the system. Each fiducial member can include a portion adapted to be sensed by a computer-aided surgical navigation system, such as a fiducial marker or marker element. Furthermore, the reference array input device can also include a plurality of indication detectors, such as a first, second, and third indication detector, capable of facilitating selection of a corresponding instruction associated with the computer-aided surgical navigation system. Moreover, the reference array input device can include a mount adapted to support the reference array input device adjacent to an object.

Block 702 is followed by block 704, in which a navigational array is mounted adjacent to a joint replacement prosthesis. A joint replacement prosthesis can include, but is not limited to, a tibial component, and a femoral component.

Block 704 is followed by block 706, in which a portion of at least three of the fiducial members can be sensed by a computer-aided surgical navigation system.

Block 706 is followed by block 708, in which a position associated with the joint replacement prosthesis is determined based in part on sensing the portions of the at least three of the fiducial members.

Block 708 is followed by block 710, in which at least one of the indication detectors is selected, whereby a corresponding instruction is received by the computer-aided surgical navigation system.

Block 710 is followed by block 712, in which the joint replacement prosthesis is mounted to another corresponding joint replacement prosthesis for a joint replacement.

At block 712, the method 700 ends.

Changes and modifications, additions and deletions may be made to the structures and methods recited above and shown in the drawings without departing from the scope of the invention and the following claims.

What is claimed is:

1. A system comprising a reference array input device and a computer-aided surgical navigation system, wherein the reference array input device can be sensed by at least two sensors associated with the computer-aided surgical navigation system, and wherein a relative position and orientation associated with the reference array input device may be determined by the computer-aided surgical navigation system, the reference array input device comprising:
   (a) a plurality of fiducial markers positioned on the reference array input device and adapted to be sensed by the computer-aided surgical navigation system, wherein a position and orientation associated with the reference array input device can be determined when at least some of the fiducial markers are sensed by the computer-aided surgical navigation system;
   (b) at least one indication detector positioned on the reference array input device, wherein a positioning of a first object at said at least one indication detector indicates at least one instruction for execution by the computer-aided surgical navigation system; and
   (c) a mount adapted to support the reference array input device adjacent to a second object.

2. The system of claim 1, wherein at least three of the fiducial markers are oriented in a flat, coplanar, Y-shaped configuration.

3. The system of claim 1, wherein at least a portion of each fiducial markers can be sensed by the computer-aided surgical navigation system using at least one of the following: infrared, sound, visual, magnetic, electromagnetic, and x-ray.

4. The system of claim 3, wherein the fiducial markers can be at least one of the following: a geometric shape, a sphere, a block, and a plate.

5. The system of claim 1, wherein the at least one indication detector can comprise at least one of the following: an input button, an input device, a contact device, a sensor device, a detector device, a transmitter device, a receiver device, or an infrared device.

6. The system of claim 1, wherein the at least one indication detector comprises an identification indicator.

7. The system of claim 6, wherein the identification indicator can comprise at least one of the following: a triangle, a square, a circle, a star, a polygon, an oval, a unique geometrical shape, a number, a letter, alphanumeric text, a symbol, a color.

8. The system of claim 1, wherein the instruction for the computer-aided surgical navigation system can comprise at least one of the following: a tab command, a focus command, a select command, an increment function, a decrement function, a forward function, a backward function, a functional command, a function, an operational command, an operation.

9. The system of claim 1, wherein the instruction for the computer-aided surgical navigation system is associated with at least one of the following: a size selection, a shape selection, a numeric selection, an alphanumeric selection, a selection of a range of sizes, a selection of a range of numbers, a material selection, a body component selection, an orthopedic component selection, or a surgical procedure selection.

10. The system of claim 1, wherein the first object comprises a probe.

11. The system of claim 1, wherein the mount comprises at least one of the following: a pronged connector, a magnet, a threaded connector, an adhesive, and a bone screw.

12. A method for performing a surgical procedure using a reference array input device and a computer-aided surgical navigation system, wherein the reference array input device can be sensed by at least two sensors associated with the computer-aided surgical navigation system, and wherein a relative position and orientation of the reference array input device may be determined by the computer-aided surgical navigation system, the method comprising:
   (a) mounting a reference array input device adjacent to a first object, wherein the reference array input device comprises:
      (i) a plurality of fiducial markers positioned on the reference array input device and adapted to be sensed by the computer-aided surgical navigation system, wherein a position and orientation associated with the reference array input device can be determined when at least some of the fiducial markers are sensed by the computer-aided surgical navigation system;
      (ii) at least one indication detector positioned on the reference array input device; and
      (iii) a mount adapted to support the reference array input device adjacent to the first object;
   (b) sensing the relative position and orientation of the reference array input device by the computer-aided surgical navigation system;
   (c) determining a position associated with the first object based in part on sensing the relative position and orientation of the reference array input device; and
   (d) positioning a second object at the indication detector to select at least one corresponding instruction for execution by the computer-aided surgical navigation system.

13. The method of claim 12, wherein at least three of the fiducial markers are oriented in a flat, coplanar, Y-shaped configuration.

14. The method of claim 12, wherein at least a portion of each fiducial marker can be sensed by the computer-aided surgical navigation system using at least one of the following: infrared, sound, visual, magnetic, electromagnetic, and x-ray.

15. The method of claim 14, wherein the fiducial markers can be at least one of the following: a geometric shape, a sphere, a block, and a plate.

16. The method of claim 14, wherein the indication detector can comprise at least one of the following: an input button, an input device, a contact device, a sensor device, a detector device, a transmitter device, a receiver device, or an infrared device.

17. The method of claim 14, wherein the indication detector can further comprise an identification indicator.

18. The method of claim 17, wherein the identification indicator can comprise at least one of the following: a triangle, a square, a circle, a star, a polygon, an oval, a unique geometrical shape, a number, a letter, alphanumeric text, a symbol, a color.

19. The method of claim 14, wherein the instruction for a computer-aided surgical navigation system can comprise at least one of the following: a tab command, an increment function, a decrement function, a forward function, a backward function, a functional command, a function, an operational command, an operation.

20. The method of claim 14, wherein the instruction for the computer-aided surgical navigation system is associated with at least one of the following: a size selection, a shape selection, a numeric selection, an alphanumeric selection, a selection of a range of sizes, a selection of a range of numbers, a material selection, a body component selection, an orthopedic component selection, or a surgical procedure selection.

21. The method of claim 14, wherein the mount comprises at least one of the following: a pronged connector, a magnet, a threaded connector, an adhesive, and a bone screw.

22. The method of claim 12, wherein the second object comprises a probe.

23. An input system comprising:
 (a) a computer-aided navigation system;
 (b) a surgical instrument; and
 (c) a reference array input device comprising:
  (i) a plurality of fiducial markers positioned on the reference array input device and adapted to be sensed by the computer-aided surgical navigation system, wherein a position and orientation of the reference array input device can be determined from sensing at least some of the fiducial markers by the computer-aided surgical navigation system;
  (ii) at least one indication detector positioned on the reference array input device, wherein positioning the surgical instrument at the at least one indication detector indicates at least one instruction for execution b the computer-aided surgical navigation system; and
  (iii) a mount adapted to support the reference array input device adjacent to an object.

24. The system of claim 23, wherein at least three of the fiducial markers are oriented in a flat, coplanar, Y-shaped configuration.

25. The system of claim 23, wherein at least a portion of each fiducial marker can be sensed by the computer-aided surgical navigation system using at least one of the following: infrared, sound, visual, magnetic, electromagnetic, and x-ray.

26. The system of claim 23, further comprising a plurality of fiducial markers attached to the surgical instrument.

27. The system of claim 26, wherein the surgical instrument comprises a probe.

28. The system of claim 23, wherein the indication detector can comprise at least one of the following: an input button, an input device, a contact device, a sensor device, a detector device, a transmitter device, a receiver device, or an infrared device.

29. The system of claim 23, wherein the indication detector can further comprise an identification indicator.

30. The system of claim 29, wherein the identification indicator can comprise at least one of the following: a triangle, a square, a circle, a star, a polygon, an oval, a unique geometrical shape, a number, a letter, alphanumeric text, a symbol, a color.

31. The system of claim 23, wherein the instruction for the computer-aided surgical navigation system can comprise at least one of the following: a tab command, a focus command, a select command, an increment function, a decrement function, a forward function, a backward function, a functional command, a function, an operational command, an operation.

32. The system of claim 23, wherein the instruction for a computer-aided surgical navigation system is associated with at least one of the following: a size selection, a shape selection, a numeric selection, an alphanumeric selection, a selection of a range of sizes, a selection of a range of numbers, a material selection, a body component selection, an orthopedic component selection, or a surgical procedure selection.

33. The system of claim 23, wherein the mount can be mounted to at least one of the following: a portion of a patient's body, a second surgical instrument, a surgical item, an item associated with a surgery.

34. The system of claim 23, wherein the mount comprises at least one of the following: a pronged connector, a magnet, a threaded connector, an adhesive, and a bone screw.

35. A method for performing a surgical procedure using an input system and a computer-aided surgical navigation system, the method comprising:
 (a) mounting a reference array input device adjacent to a first surgical instrument, wherein the reference array input device comprises:
  (i) a plurality of fiducial markers positioned on the reference array input device and adapted to be sensed by the computer-aided surgical navigation system, wherein a relative position and orientation associated with the reference array input device can be determined from sensing at least some of the fiducial markers by the computer-aided surgical navigation system;
  (ii) at least one indication detector positioned on the reference array input device; and
  (iii) a mount adapted to support the reference array input device adjacent to the first surgical instrument;
 (b) sensing a portion of at least three of the fiducial markers by the computer-aided surgical navigation system;
 (c) determining a position associated with the first surgical instrument based in part on sensing the portions of the at least three of the fiducial markers; and
 (d) positioning a second surgical instrument at the at least one indication detector to indicate at least one corresponding instruction for execution by the computer-aided surgical navigation system.

36. The method of claim 35, wherein at least three of the fiducial markers are oriented in a flat, coplanar, Y-shaped configuration.

37. The method of claim 35, wherein at least a portion of each fiducial marker can be sensed by the computer-aided surgical navigation system using at least one of the following: infrared, sound, visual, magnetic, electromagnetic, and x-ray.

38. The method of claim 37, wherein the fiducial markers can be at least one of the following: a geometric shape, a sphere, a block, and a plate.

39. The method of claim 35, wherein the at least one indication detector can comprise at least one of the following: an input button, an input device, a contact device, a sensor device, a detector device, a transmitter device, a receiver device, or an infrared device.

40. The method of claim 35, wherein the at least one indication detector can further comprise an identification indicator.

41. The method of claim 40, wherein the identification indicator can comprise at least one of the following: a triangle, a square, a circle, a star, a polygon, an oval, a unique geometrical shape, a number, a letter, alphanumeric text, a symbol, a color.

42. The method of claim 35, wherein the instruction for the computer-aided surgical navigation system can comprise at least one of the following: a tab command, a focus command, a select command, an increment function, a decrement function, a forward function, a backward function, a functional command, a function, an operational command, an operation.

43. The method of claim 35, wherein the instruction for the computer-aided surgical navigation system is associated with at least one of the following: a size selection, a shape selection, a numeric selection, an alphanumeric selection, a selection of a range of sizes, a selection of a range of numbers, a material selection, a body component selection, an orthopedic component selection, or a surgical procedure selection.

44. The method of claim 35, wherein the mount comprises at least one of the following: a pronged connector, a magnet, a threaded connector, an adhesive, and a bone screw.

45. The method of claim 35, wherein the first surgical instrument comprises at least one of the following: a surgical implement, a surgical reference, a surgical trial, an implant, a cutting block, a reamer, a drill, a saw, an extramedullary rod, and an intramedullar rod.

46. The method of claim 35, wherein the second surgical instrument comprises a probe.

* * * * *